US007418351B2

(12) United States Patent
Weng

(10) Patent No.: US 7,418,351 B2
(45) Date of Patent: Aug. 26, 2008

(54) METHODS FOR ANALYSIS OF MEASUREMENT ERRORS IN MEASURED SIGNALS

(75) Inventor: Lee Weng, Bellevue, WA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 1166 days.

(21) Appl. No.: 10/354,664

(22) Filed: Jan. 30, 2003

(65) Prior Publication Data

US 2003/0226098 A1 Dec. 4, 2003

Related U.S. Application Data

(60) Provisional application No. 60/353,845, filed on Jan. 31, 2002.

(51) Int. Cl.
*G06F 19/00* (2006.01)
(52) U.S. Cl. ...................................... 702/19
(58) Field of Classification Search ............ 702/19
See application file for complete search history.

(56) References Cited

U.S. PATENT DOCUMENTS

| 5,510,270 | A | 4/1996 | Fodor et al. |
| 5,539,083 | A | 7/1996 | Cook et al. |
| 5,545,522 | A | 8/1996 | Van Gelder et al. |
| 5,556,752 | A | 9/1996 | Lockhart et al. |
| 5,569,588 | A | 10/1996 | Ashby et al. |
| 5,578,832 | A | 11/1996 | Trulson et al. |
| 5,716,785 | A | 2/1998 | Van Gelder et al. |
| 5,891,636 | A | 4/1999 | Van Gelder et al. |
| 6,028,189 | A | 2/2000 | Blanchard |
| 6,040,138 | A * | 3/2000 | Lockhart et al. ........ 435/6 |
| 6,132,997 | A | 10/2000 | Shannon |
| 6,218,122 | B1 | 4/2001 | Friend et al. |
| 6,271,002 | B1 | 8/2001 | Linsley et al. |
| 6,351,712 | B1 * | 2/2002 | Stoughton et al. ....... 702/19 |

(Continued)

FOREIGN PATENT DOCUMENTS

EP 534858 9/1992

(Continued)

OTHER PUBLICATIONS

Bass et al., 2000, "Double-stranded RNA as a template for gene silencing" Cell (101):235-238.

(Continued)

*Primary Examiner*—John E Barlow, Jr.
*Assistant Examiner*—Jonathan Moffat
(74) *Attorney, Agent, or Firm*—Jones Day

(57) ABSTRACT

The present invention provides methods for analyzing measurement errors in measured signals obtained in an experiment, e.g., measured intensity signals obtained in a microarray gene expression experiment. In particular, the invention provides a method for transforming measured signals into a domain in which the measurement errors in the transformed signals are normalized by errors as determined from an error model. The methods of the invention are particularly useful for analyzing measurement errors in signals in which at least portion of the error is dependent on the magnitudes of the signals. Such transformed signals permit analysis of data using traditional statistical methods, e.g., ANOVA and regression analysis. Magnitude-independent errors can also be used for comparing level of measurement errors in signals of different magnitudes.

42 Claims, 14 Drawing Sheets

U.S. PATENT DOCUMENTS

| | | | |
|---|---|---|---|
| 6,713,257 B2 | 3/2004 | Shoemaker et al. | |
| 7,003,403 B1 * | 2/2006 | Dougherty et al. | 702/19 |
| 2004/0143399 A1 | 7/2004 | Weng | |

FOREIGN PATENT DOCUMENTS

| | | |
|---|---|---|
| WO | WO 90/11364 | 10/1990 |
| WO | WO 98/38329 | 9/1998 |
| WO | WO 98/41531 | 9/1998 |
| WO | WO99/58708 | 11/1999 |
| WO | WO99/59037 | 11/1999 |
| WO | WO 99/66067 | 12/1999 |
| WO | WO 00/24936 | 5/2000 |
| WO | WO 00/39336 | 7/2000 |
| WO | WO 00/39339 | 7/2000 |
| WO | WO 02/16650 | 2/2002 |

OTHER PUBLICATIONS

Belshaw et al., 1996, "Controlling protein association and subcellular localization with a synthetic ligand that induces heterodimerization of proteins" Proc Natl Acad Sci U S A (93):4604-7.

Blanchard et al., 1996, "High-density oligonucleotide arrays" Biosensors & Bioelectronics (11):687-690.

Blanchard et al., 1998, "Synthetic DNA Arrays" Genetic Engineering (0):111-123.

Blanchard al., 1996, "Sequence to array: probing the genome's secrets" Nat Biotechnol (14):1649-0.

Cech et al., 1987, "The chemistry of self-splicing RNA and RNA enzymes" Science (236):1532-1539.

Chirgwin et al., 1979, "Isolation of biologically active ribonucleic acid from sources enriched in ribonuclease" Biochemistry (18):5294-5299.

Crollius et al., 2000, "Estimate of human gene number provided by genomewide analysis using Tetraodon nigroviridis DNA sequence" Nat Genet (25):235-238.

De Wildt et al., 2000, "Antibody arrays for high-throughput screening of antibody-antigen interactions" Nat Biotechnol (18):989-994.

DeRisi et al., 1996, "Use of a cDNA microarray to analyse gene expression patterns in human cancer" Nat Genet (14):457-60.

Dohmen et al., 1994, "Heat-inducible degron: a method for constructing temperature-sensitive mutants" Science (263):1273-6.

Duggan et al., 1999, "Expression profiling using cDNA microarrays" Nat Genet (21):10-4.

Egholm et al., 1993, "PNA hybridizes to complementary oligonucleotides obeying the Watson-Crick hydrogen-bonding rules," Nature (365):566-8.

Elbashir et al., 2001, "Duplexes of 21-nucleotide RNAs mediate RNA interference in cultured mammalian cells" Nature (411):494-498.

Ewing et al., 2000, "Analysis of expressed sequence tags indicates 35,000 human genes" Nat Genet (25):232-234.

Ferguson et al., 1996, "A fiber-optic DNA biosensor microarray for the analysis of gene expression" Nat Biotechnol(14): 1681-4.

Fire et al., 1998, "Potent and specific genetic interference by double-stranded RNA in Caenorhabditis elegans" Nature (391):806-811.

Fodor et al., 1991, "Light-directed, spatially addressable parallel chemical synthesis" Science (251):767-773.

Froehler et al., 1986, "Synthesis of DNA via deoxynucleoside H-phosphonate intermediates" Nucleic Acids Res (14):5399-5407.

Gibson et al., 1996, "Antisense approaches to the gene therapy of cancer—Recnac" Cancer Metastasis Rev (15):287-99.

Goffeau et al., 1996, "Life with 6000 genes" Science (274):546-567.

Good et al., 1997, "Expression of small, therapeutic RNAs in human cell nuclei" Gene Ther (4):45-54.

Gossen et al., 1992, "Tight control of gene expression in mammalian cells by tetracycline-responsive promoters" Proc Natl Acad Sci U S A (89):5547-51.

Grant et al., 1999, "Dissecting the mechanisms of posttranscriptional gene silencing: divide and conquer" Cell (96):303-306.

Grassi et al., 1996, "Ribozymes: structure, function, and potential therapy for dominant genetic disorders" Ann Med (28):499-510.

Guo et al., 1995, "par-1, a gene required for establishing polarity in C. elegans embryos, encodes a putative Ser/Thr kinase that is asymmetrically distributed" Cell (81):611-620.

Gygi et al., 1999, "Quantitative analysis of complex protein mixtures using isotope-coded affinity tags" Nat Biotechnol (17):994-999.

Haseloff et al., 1988, "Simple RNA enzymes with new and highly specific endoribonuclease activities" Nature (334):585-591.

Hoffmann et al., 1997, "A novel tetracycline-dependent expression vector with low basal expression and potent regulatory properties in various mammalian cell lines" Nucleic Acids Res (25): 1078-9.

Hofmann et al., 1996, "Rapid retroviral delivery of tetracycline-inducible genes in a single autoregulatory cassette" Proc Natl Acad Sci U S A (93):5185-5190.

Holder et al., 2001, "Quantitation of Gene Expression for High-Density Oligonucleotide Arrays: A Safer Approach" Genelogic Workshop on Low Level Analysis of Affymetrix Genechip® data p. 1-32.

Koizumi et al., 1988, "Construction of a series of several self-cleaving RNA duplexes using synthetic 21-mers" FEBS Lett (228):228-230.

Lander et al., 1996, "The new genomics: global views of biology" Science (274):536-539.

Lockhart et al., 1996, "Expression monitoring by hybridization to high-density oligonucleotide arrays" Nat Biotechnol (14):1675-80.

MacBeath et al., 2000, "Printing proteins as microarrays for high-throughput function determination" Science (289): 1760-1763.

Maskos et al., 1992, "Oligonucleotide hybridizations on glass supports: a novel linker for oligonucleotide synthesis and hybridization properties of oligonucleotides synthesised in situ" Nucleic Acids Res (20):1679-84.

McBride et al., 1983, "An investigation of several deoxynucleoside phosphoramidites useful for synthesizing deoxyoligonucleotides", Tetrahedron Lett. 24:246-248.

McGall et al., 1996, "Light-directed synthesis of high-density oligonucleotide arrays using semiconductor photoresists" Proc Natl Acad Sci U S A (93):13555-60.

Nguyen et al., 1995, "Differential gene expression in the murine thymus assayed by quantitative hybridization of arrayed cDNA clones" Genomics (29):207-16.

No et al., 1996, "Ecdysone-inducible gene expression in mammalian cells and transgenic mice" Proc Natl Acad Sci U S A (93):3346-3351.

Paddison et al., 2002, "Stable suppression of gene expression by RNAi in mammalian cells" Proc Natl Acad Sci U S A (99): 1443-1148.

Paulus et al., 1996, "Self-contained, tetracycline-regulated retroviral vector system for gene delivery to mammalian cells" J Virol (70):62-67.

Pease et al., 1994, "Light-generated oligonucleotide arrays for rapid DNA sequence analysis" Proc Natl Acad Sci U S A (91):5022-5026.

Petcherski et al., 2000, "LAG-3 is a putative transcriptional activator in the C. elegans Notch pathway" Nature (405):364-368.

Prashar et al., 1996, "Analysis of differential gene expression by display of 3' end restriction fragments of cDNAs" Proc Natl Acad Sci U S A (93):659-663.

Roberts et al., 2000, "Signaling and circuitry of multiple MAPK pathways revealed by a matrix of global gene expression profiles" Science (287):873-880.

Rocke et al., 2001, "A model for measurement error for gene expression arrays" J Comput Biol (8):557-569.

Sagliocco et al., 1996, "Identification of proteins of the yeast protein map using genetically manipulated strains and peptide-mass fingerprinting" Yeast (12):1519-1533.

Sarver et al., 1990, "Ribozymes as potential anti-HIV-1 therapeutic agents" Science (247):1222-1225.

Schena et al., 1996, "Parallel human genome analysis: microarray-based expression monitoring of 1000 genes" Proc Natl Acad Sci U S A (93):10614-9.

Schena et al., 1995, "Quantitative monitoring of gene expression patterns with a complementary DNA microarray" Science (270):467-470.

Shalon et al., 1996, "A DNA microarray system for analyzing complex DNA samples using two-color fluorescent probe hybridization" Genome Res (6):639-45.

Shevchenko et al., 1996, "Linking genome and proteome by mass spectrometry: large-scale identification of yeast proteins from two dimensional gels" Proc Natl Acad Sci U S A (93): 14440-14445.

Spencer et al., 1996, "Creating conditional mutations in mammals" Trends Genet (12):181-187.

Tabara et al., 1999, "The rde-1 gene, RNA interference, and transposon silencing in *C. elegans*" Cell (99):123-32.

Velculescu et al., 1995, "Serial analysis of gene expression" Science (270):484-487.

Zamore et al., 2000, "RNAi: double-stranded RNA directs the ATP-dependent cleavage of mRNA at 21 to 23 nucleotide intervals" Cell (101):25-33.

Zhu et al., 2001, "Global analysis of protein activities using proteome chips" Science (293):2101-2105.

Munson, 2001, "A 'Consistency' Test for Determining the Significance of Gene Expression Changes on Replicate Samples and Two Convenient Variance-Stabilizing Transformations" [online]. [Retrieved Nov. 12, 2004]. Retrieved from the Internet: <URL: http://www.stat.berkeley.edu/users/terry/zarray/Affy/GL_Workshop/Munson.ppt>.

Durbin et al., 2002, "A Variance-Stabilizing Transformation for Gene-Expression Microarray Data" Bioinformatics, vol. 18 Suppl. 1 2002, S105-S110.

Huber et al., 2002, "Variance Stabilization Applied to Microarray Data Calibration and to the Quantification of Differential Expression" Bioinformatics, vol. 18 Suppl 1 2002, S96-S104.

\* cited by examiner

METHODS FOR ANALYSIS OF MEASUREMENT ERRORS IN MEASURED SIGNALS

This application claims benefit, under 35 U.S.C. §119(e), of U.S. Provisional Patent Application No. 60/353,845, filed on Jan. 31, 2002, which is incorporated herein by reference in its entirety.

1. FIELD OF THE INVENTION

The present invention relates to methods of analyzing measurement errors in measured signals. The invention also relates to methods for analyzing measured signals and methods of processing measured signals, such as methods of obtaining difference of measured signals, methods of obtaining error-weighted averages, and methods of identifying and removing outliers.

2. BACKGROUND OF THE INVENTION

DNA array technologies have made it possible to monitor the expression level of a large number of genetic transcripts at any one time (see, e.g., Schena et al., 1995, Science 270:467-470; Lockhart et al., 1996, Nature Biotechnology 14:1675-1680; Blanchard et al., 1996, Nature Biotechnology 14:1649; Ashby et al., U.S. Pat. No. 5,569,588, issued Oct. 29, 1996). Of the two main formats of DNA arrays, spotted cDNA arrays are prepared by depositing PCR products of cDNA fragments with sizes ranging from about 0.6 to 2.4 kb, from full length cDNAs, ESTs, etc., onto a suitable surface (see, e.g., DeRisi et al., 1996, Nature Genetics 14:457-460; Shalon et al., 1996, Genome Res. 6:689-645; Schena et al., 1995, Proc. Natl. Acad. Sci. U.S.A. 93:10539-11286; and Duggan et al., Nature Genetics Supplement 21:10-14). Alternatively, high-density oligonucleotide arrays containing thousands of oligonucleotides complementary to defined sequences, at defined locations on a surface are synthesized in situ on the surface by, for example, photolithographic techniques (see, e.g., Fodor et al., 1991, Science 251:767-773; Pease et al., 1994, Proc. Natl. Acad. Sci. U.S.A. 91:5022-5026; Lockhart et al., 1996, Nature Biotechnology 14:1675; McGall et al., 1996, Proc. Natl. Acad. Sci. U.S.A. 93:13555-13560; U.S. Pat. Nos. 5,578,832; 5,556,752; 5,510,270; and 6,040,138). Methods for generating arrays using inkjet technology for in situ oligonucleotide synthesis are also known in the art (see, e.g., Blanchard, International Patent Publication WO 98/41531, published Sep. 24, 1998, Blanchard et al., 1996, Biosensors and Bioelectronics 11:687-690; Blanchard, 1998, in Synthetic DNA Arrays in Genetic Engineering, Vol. 20, J. K. Setlow, Ed., Plenum Press, New York at pages 111-123). Efforts to further increase the information capacity of DNA arrays range from further reducing feature size on DNA arrays so as to further increase the number of probes in a given surface area to sensitivity- and specificity-based probe design and selection aimed at reducing the number of redundant probes needed for the detection of each target nucleic acid thereby increasing the number of target nucleic acids monitored without increasing probe density (see, e.g., Friend et al., U.S. patent application Ser. No. 09/364,751, filed on Jul. 30, 1999; and Friend et al., U.S. patent application Ser. No. 09/561,487, filed on Apr. 28, 2000).

By simultaneously monitoring tens of thousands of genes, DNA array technologies have allowed, inter alia, genome-wide analysis of mRNA expression in a cell or a cell type or any biological sample. Aided by sophisticated data management and analysis methodologies, the transcriptional state of a cell or cell type as well as changes of the transcriptional state in response to external perturbations, including but not limited to drug perturbations, can be characterized on the mRNA level (see, e.g., Stoughton et al., International Publication No. WO 00/39336, published Jul. 6, 2000; Friend et al., International Publication No. WO 00/24936, published May 4, 2000). Applications of such technologies include, for example, identification of genes which are up regulated or down regulated in various physiological states, particularly diseased states. Additional exemplary uses for DNA arrays include the analyses of members of signaling pathways, and the identification of targets for various drugs. See, e.g., Friend and Hartwell, International Publication No. WO 98/38329 (published Sep. 3, 1998); Stoughton, International Publication No. WO 99/66067 (published Dec. 23, 1999); Stoughton and Friend, International Publication No. WO 99/58708 (published Nov. 18, 1999); Friend and Stoughton, International Publication No. WO 99/59037 (published Nov. 18, 1999); Friend et al., U.S. patent application Ser. No. 09/334,328 (filed on Jun. 16, 1999).

The various characteristics of this analytic method make it particularly useful for directly comparing the abundance of mRNAs present in two cell types. For example, an array of cDNAs was hybridized with a green fluor-tagged representation of mRNAs extracted from a tumorigenic melanoma cell line (UACC-903) and a red fluor-tagged representation of mRNAs was extracted from a nontumorigenic derivative of the original cell line (UACC-903+6). Monochrome images of the fluorescent intensity observed for each of the fluors were then combined by placing each image in the appropriate color channel of a red-green-blue (RGB) image. In this composite image, one can see the differential expression of genes in the two cell lines. Intense red fluorescence at a spot indicates a high level of expression of that gene in the nontumorigenic cell line, with little expression of the same gene in the tumorigenic parent. Conversely, intense green fluorescence at a spot indicates high expression of that gene in the tumorigenic line, with little expression in the nontumorigenic daughter line. When both cell lines express a gene at similar levels, the observed array spot is yellow. Such a method is often termed "two-channel" measurement as compared to a method in which only one color labeling is measured.

Any quantitative measurement method, if affected by measurement errors, will have uncertainties in the measurement results. DNA microarray technology is not an exception. Differential expression ratios are typically derived from measured intensities in both single-channel and two-channel microarray technologies, so that it is essential to understand the intensity measurement errors. Measurement errors are often described by error models (see, e.g., Supplementary material to Roberts et al, 2000, Science, 287:873-880; and Rocke et al., 2001, J. Computational Biology 8:557-569). In a two-term error model, the first error source is a low-level additive noise of constant variance, which comes from the background of the array chip. This constant noise is independent from the hybridization levels of individual feature spots on a microarray. It may come from the combination of the scanner electronics noise and the chip surface fluorescence due to nonspecific binding. This constant additive noise is typically assumed normally distributed with a mean background. After background level subtraction, which is typically carried out during microarray data processing, the additive mean background becomes zero. The second error source is a multiplicative error that is the combined result of the speckle noise inherent in the coherent laser scanner and the fluorescent dye related noise. The multiplicative error is also called fractional error because its level is directly proportional to the measured intensity level. It is the dominant error source at high intensity levels. Sometimes an extra square-root term is also included to describe the effect of variation in number of available binding sites in a spot. This term is also called the Poisson term, because it is believed that the number of binding sites follows a Poisson distribution, and has a variance which is proportional to the average number of binding of sites.

Many microarray data processing and statistical analysis methods require the variance of the measurement error to be constant. In other words, the measurement variance should not be related to the measurement level over a measurement range. For example, in the commonly used analysis of variance (ANOVA) method, the variables under investigation must have a constant variance. In another example, many data regression and parametric or non-parametric modeling methods used in microarray data normalization and detrending to remove the intensity dependent non-linearity have the underlying assumptions that the data is not heteroskedastic (i.e., not having a changing variance). However, due to the multiplicative and Poisson terms, the measured microarray intensities do not meet the constant-variance requirement. To overcome thisproblem, measured intensities are often transformed to a new domain where the variance becomes a constant. All analysis and data processing are then carried out in the transformed domain. A logarithmic conversion is commonly used to transform multiplicative error to constant variance. But it does not work properly in low intensities where the original additive constant noise dominates. In a piecewise hybrid transformation method, a log transform is applied to high intensities and a linear transform is applied to low intensities. It has better error characteristics near the low intensity end than the simple logarithmic conversion. But the measurement variance of the hybrid-transformed intensity is still not close to a constant. The hybrid-transform can also significantly distort intensity distributions.

There is therefore a need for more efficient method that can be used to characterize measurement errors in measured signals. In particular, these is a need for methods that transform measured signals into a transformed domain which facilitate analysis of the signals and their errors. There is also a need for more efficient methods for analyzing measured signals as well as more efficient methods for processing measured signals, such as methods of obtaining difference of measured signals, methods of obtaining error-weighted averages, and methods of identifying and removing outliers.

Discussion or citation of a reference herein shall not be construed as an admission that such reference is prior art to the present invention.

3. SUMMARY OF THE INVENTION

The present invention provides methods for analyzing measurement errors in measured signals obtained in an experiment, e.g., measured intensity signals obtained in a microarray gene expression experiment or microarray proteomics experiment. Signals from any experimental measurement can be analyzed by the methods of the present invention.

In one aspect of the invention, the measurement errors in measured signals are modeled by an error model, and a transformation is used to transform measured signals into a domain in which the measurement errors in the transformed signals are measurement errors in measured signals normalized by errors as determined from the error model. In a specific embodiment, the invention provides a method for analyzing measurement errors in a set of measured signals $\{x(k)\}$ measured in an experiment, wherein k=1, 2, . . . , N, N being the number of signals in said set, said method comprising (a) transforming said set of signals using a transformation, said transformation transforming said set of measured signals into a set of transformed signals $\{y(k)\}$ such that measurement error in each of said transformed signals is said measurement error in said measured signal normalized by a modeled error in said measured signal, said modeled error being calculated using an error model of said experiment; and (b) determining errors of said set of transformed signals. In a preferred embodiment, the method for analyzing measurement errors in measured signals $\{x(k)\}$ measured in an experiment comprises (a) determining an error model for said experiment; (b) determining a modeled error in each of said measured signals, said modeled error being calculated using said error model; (c) determining a transformation for said experiment, said transformation transforming said set of measured signals into a set of transformed signals $\{y(k)\}$ such that measurement error in each of said transformed signals is said measurement error in said measured signal normalized by said modeled error of said measured signal; (d) transforming said set of signals using said transformation; and (e) determining errors in said set in transformed signals. Preferably, the error model for the experiment is a three-term error model. Preferably, in the method of the invention N is at least 10, at least 100, at least 1000, or at least 10,000.

In another aspect of the invention, the invention provides a method for determining a residue error in a measured signal x measured in an experiment, said method comprising (a) transforming said measured signal into a transformed signal y by a method comprising using a transformation as described by equation 23, infra such that the measurement error in the transformed signal y is the measurement error in the measured signal normalized by an error calculated using a three-term error model (as described by equation 16, infra) of the experiment; (b) determining an error in the transformed signal y; and (c) determining the residue error by subtracting 1 from the error of the transformed signal y. In one embodiment, the error in the measured signal is an error in the measured signal determined in the experiment. In a preferred embodiment, the error in the measured signal is the larger of an error determined in said experiment or an error calculated according to the error model.

In still another aspect of the invention, the invention provides a method for analyzing m signals m signals $\{x\}_i$ measured in m experiments, wherein i=1, 2, . . . m, said method comprising (a) transforming said set of signals into a set of transformed signals $\{y_i\}$ by a method comprising using a transformation as described by Equation 23, infra such that the measurement error in each of the transformed signals is the measurement error in the measured signal normalized by an error calculated using a three-term error model (as described by Equation 16, infra) of said experiment; (b) determining an error in each of the transformed signal $y_i$; and (c) performing analysis based on the transformed signals and their errors. In one embodiment, the error in the measured signal is an error in the measured signal determined in the experiment. In a preferred embodiment, the error in the measured signal is the larger of an error determined in the experiment or an error calculated according to the error model. In a preferred embodiment, the analysis in step (c) is carried out by performing ANOVA on the transformed signals and their errors. In another preferred embodiment, the analysis in step (c) is carried out by performing a regression analysis on the transformed signals and their errors. Preferably, a variance of the transformed signals is determined. Preferably, m is at least 2, at least 5, at least 10, at least 100, at least 1000, or at least 10,000.

The invention also provides a method for determining an error-weighted average of m signals $x_i$ measured in m replicate experiments, wherein i=1, 2, . . . m, said method comprising (a) transforming each said signal $x_i$ into a transformed signal $y_i$ by a method comprising using a transformation as described by Equation 23, infra, such that the measurement error in each of the transformed signals is the measurement error in the measured signal normalized by an error calculated using a three-term error model (as described by Equation 16, infra) of said experiment; (b) determining an error $\Delta y_i$ in each said transformed signal $y_i$; (c) determining an error-weighted transformed signal according to the equation according to equation 31, infra; and (d) transforming said error-weighted transformed signal to produce said error-weighted average by a method comprising using a transformation according to the equation 25. Preferably, m is at least 2, at least 5, at least 10, at least 100, at least 1000, or at least 10,000.

In still another aspect of the invention, the invention provides a method for determining if a measured signal x measured in an experiment is an outlier, comprising (a) transforming said measured signal into a transformed signal y by a method comprising using a transformation as described by Equation 23, infra such that the measurement error in the transformed signal y is the measurement error in the measured signal normalized by an error calculated using a three-term error model (as described by Equation 16, infra) of the experiment; (b) determining an error in the transformed signal y; and (c) comparing the error in the transformed signal y with a predetermined threshold value, wherein the measured signal is identified as an outlier if the error in the transformed signal y is greater than the threshold value. In one embodiment, the error in the measured signal is an error in the measured signal determined in the experiment. In a preferred embodiment, the error in the measured signal is the larger of an error determined in the experiment or an error calculated according to the error model.

In still another aspect of the invention, the invention provides a method of obtaining a difference of measured signals $\{x(k)\}$ measured in an experiment, wherein k=1, 2, said method comprising (a) transforming said signals into transformed signals $\{y(k)\}$ by a method comprising using a transformation as described by Equation 23, infra such that the measurement errors in the transformed signals $\{y(k)\}$ are the measurement errors in the measured signals normalized by errors calculated using a three-term error model (as described by Equation 16, infra) of the experiment; and (b) determining a difference between the transformed signals. In a preferred embodiment, the difference between the transformed signals is transformed back by an inverse transformation as described by Equation 25, infra.

Preferably, the experiment in any one of the methods of the invention is a microarray experiment. More preferably, the measured signal in any one of the methods of the invention is measured fluorescence intensity. The measured signal in any one of the methods of the invention can also be a difference between a measured fluorescence intensity of a target probe (TP) and a measured fluorescence intensity of a reference probe (RP).

The invention also provides a computer system comprising a processor, and a memory coupled to said processor and encoding one or more programs, wherein said one or more programs cause the processor to carry out any one of the methods of the invention. The invention also provides a computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out any one of the methods of the invention.

4. BRIEF DESCRIPTION OF FIGURES

Figure 6:
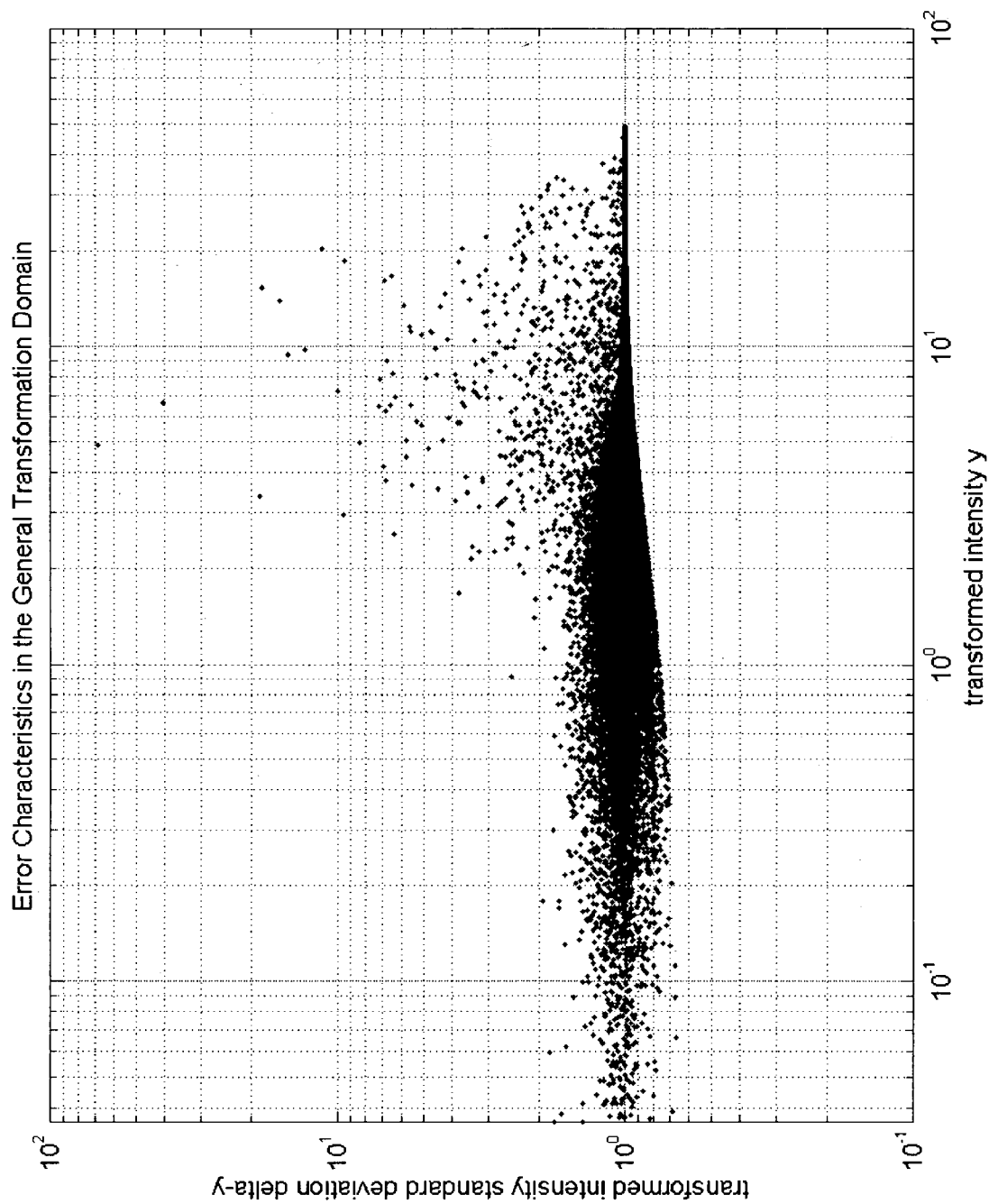

FIG. 6. The error characteristics in the general transformation domain shows the near constant relationship between the transformed intensity y and the estimated real transformed intensity standard deviation $\Delta y$ from a real testing microarray. Parameters in the transformation are a=0.1, b=3.16, c=30.1 and d=−50.8.

Figure 7:
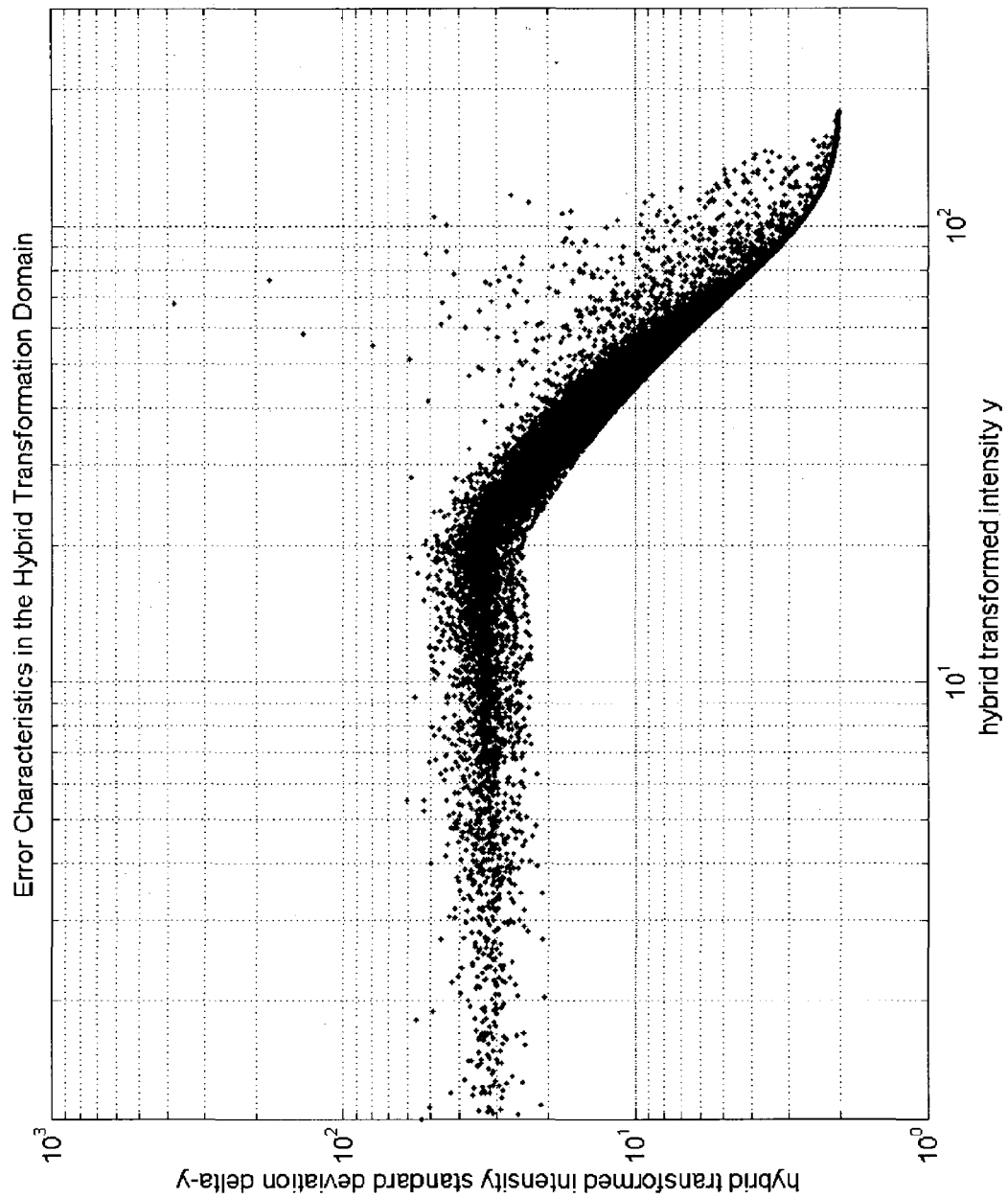

FIG. 7. The error characteristics in the hybrid transformation domain shows the non-constant relationship between the transformed intensity y and the estimated real transformed intensity standard deviation $\Delta y$ from a real testing microarray. Parameter in the transformation is c'=20.

Figure 8:
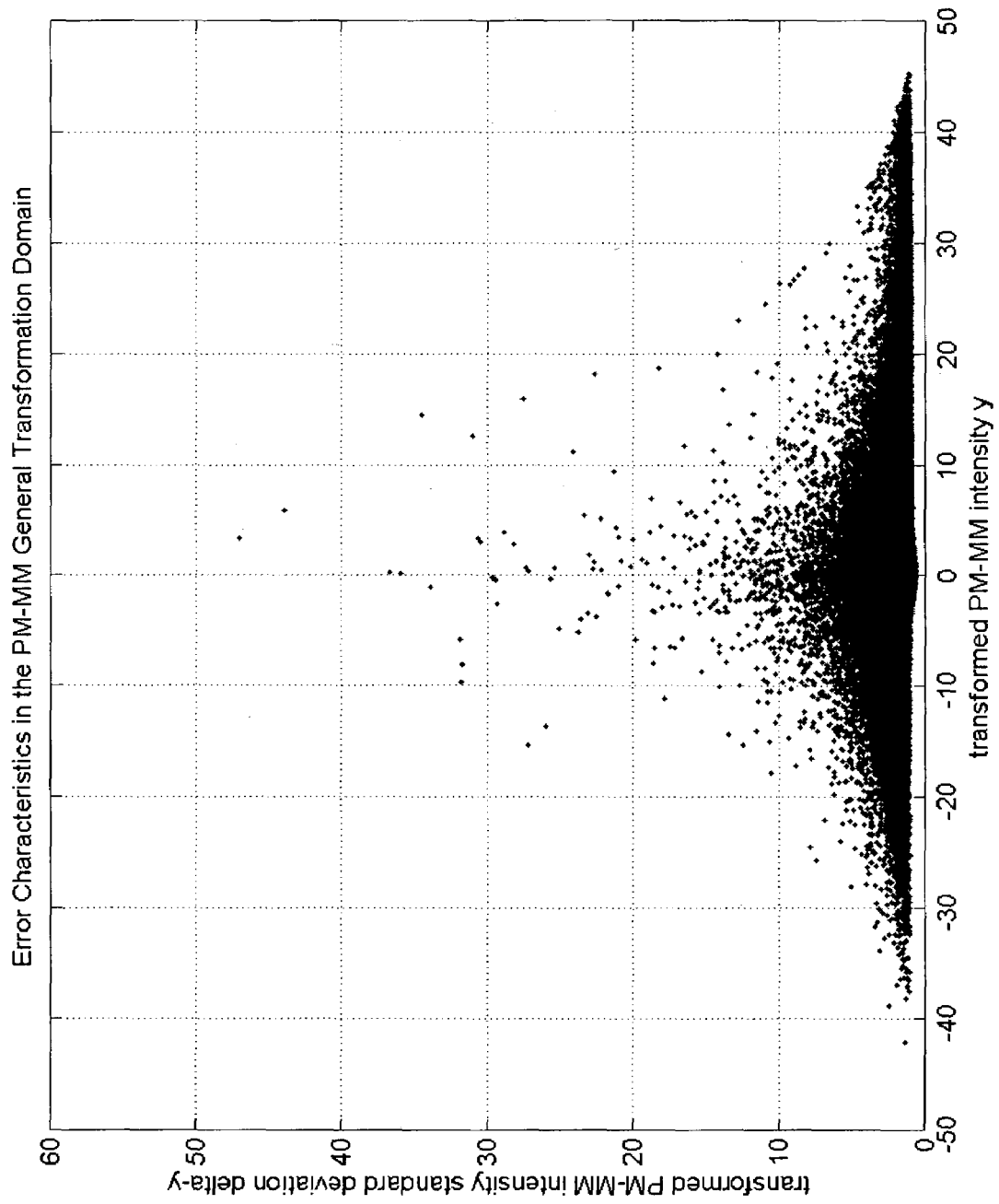

FIG. 8. The error characteristics in the PM-MM general transformation domain shows the near constant relationship between the transformed PM-MM intensity y and the stimated real transformed PM-MM intensity standard deviation $\Delta y$ from a real testing microarray. Parameters in the transformation are a=0.1, b=3.16, c=42.95 and d=−52.25.

Figure 9:
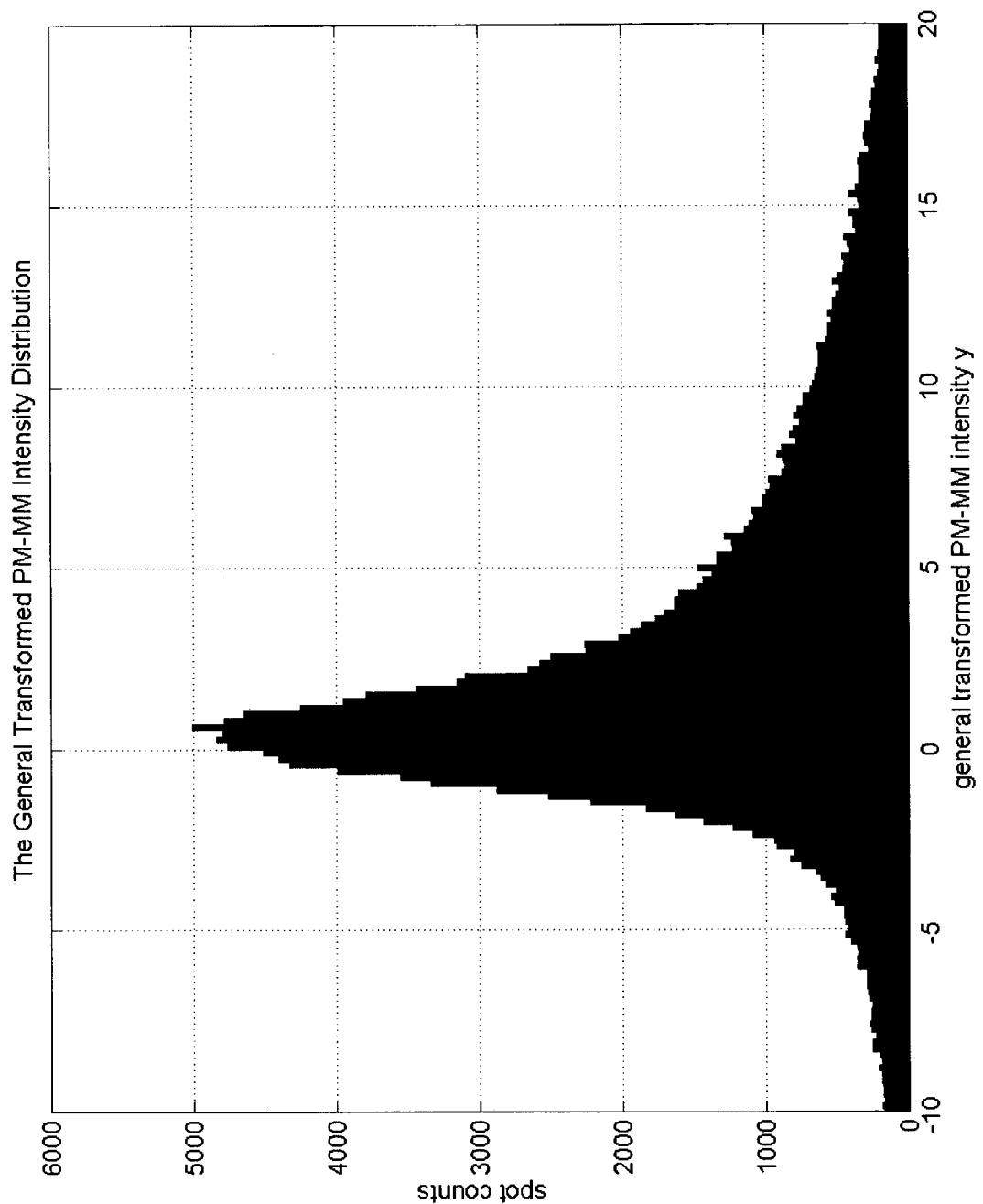

FIG. 9. The histogram of the general-transformed PM-MM intensities maintains the original shape of a smooth unimodal distribution in the original PM-MM intensity domain. Parameters in the transformation are a=0.1, b=3.16, c=42.95 and d=−52.25.

Figure 10:
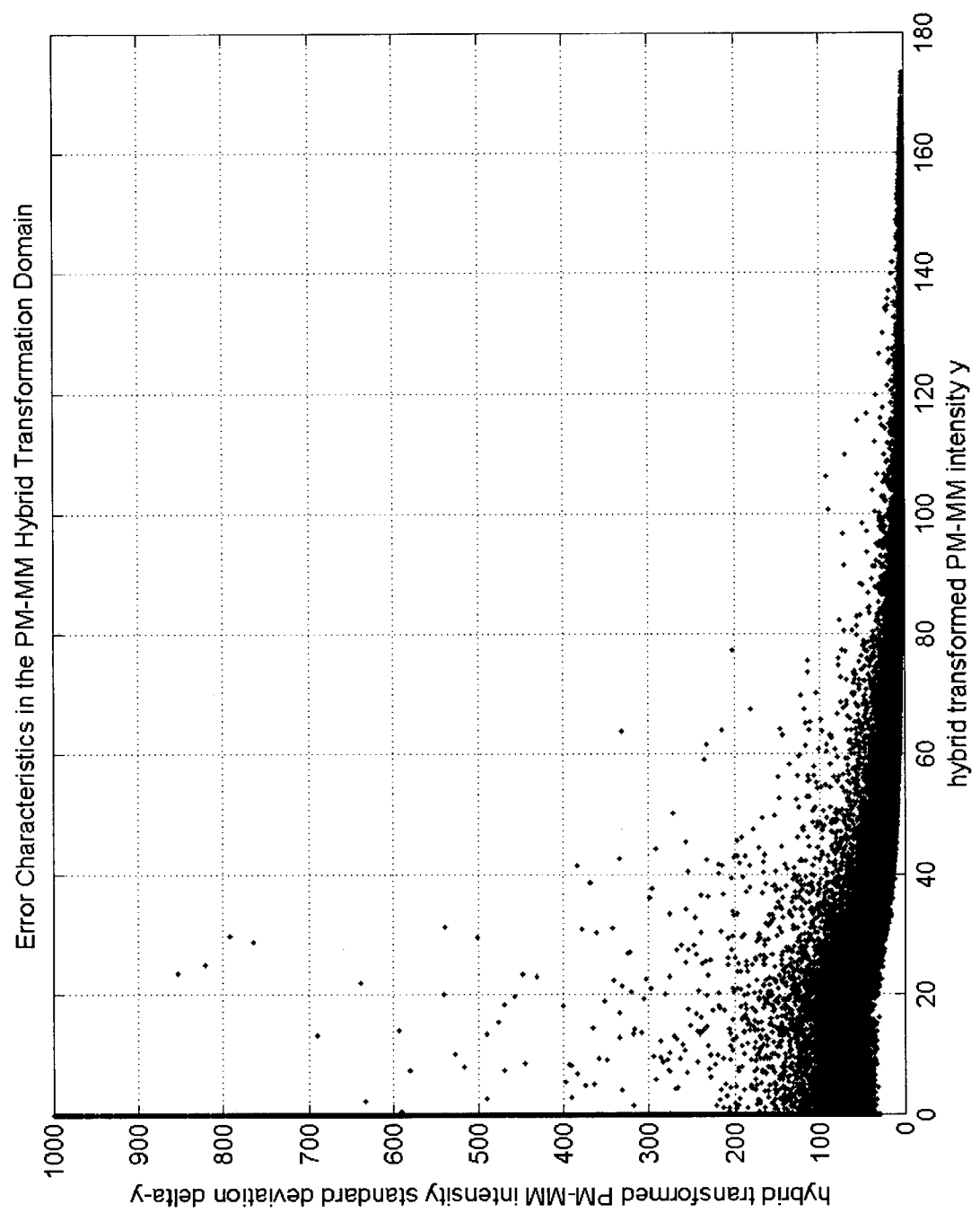

FIG. 10. The error characteristics in the PM-MM hybrid transformation domain shows the intensity-dependant trending relationship between the transformed PM-MM intensity y and the estimated real transformed PM-MM intensity standard deviation $\Delta y$ from a real testing microarray. Parameter in the transformation is c'=20.

Figure 11:
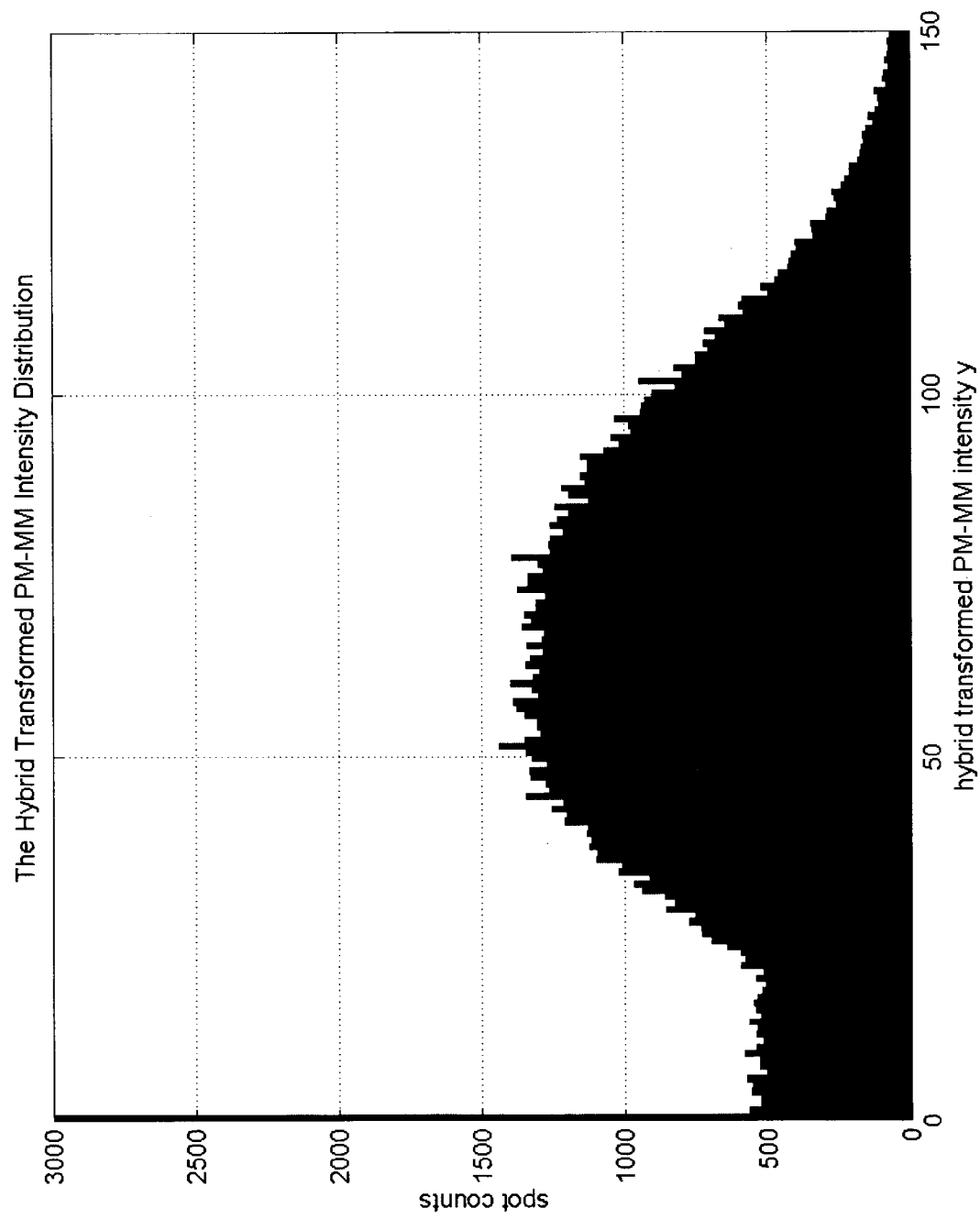

FIG. 11. The histogram of the hybrid transformed PM-MM intensity shows a sharp distribution distortion near the piecewise transition boundary c'=20.

Figure 1:
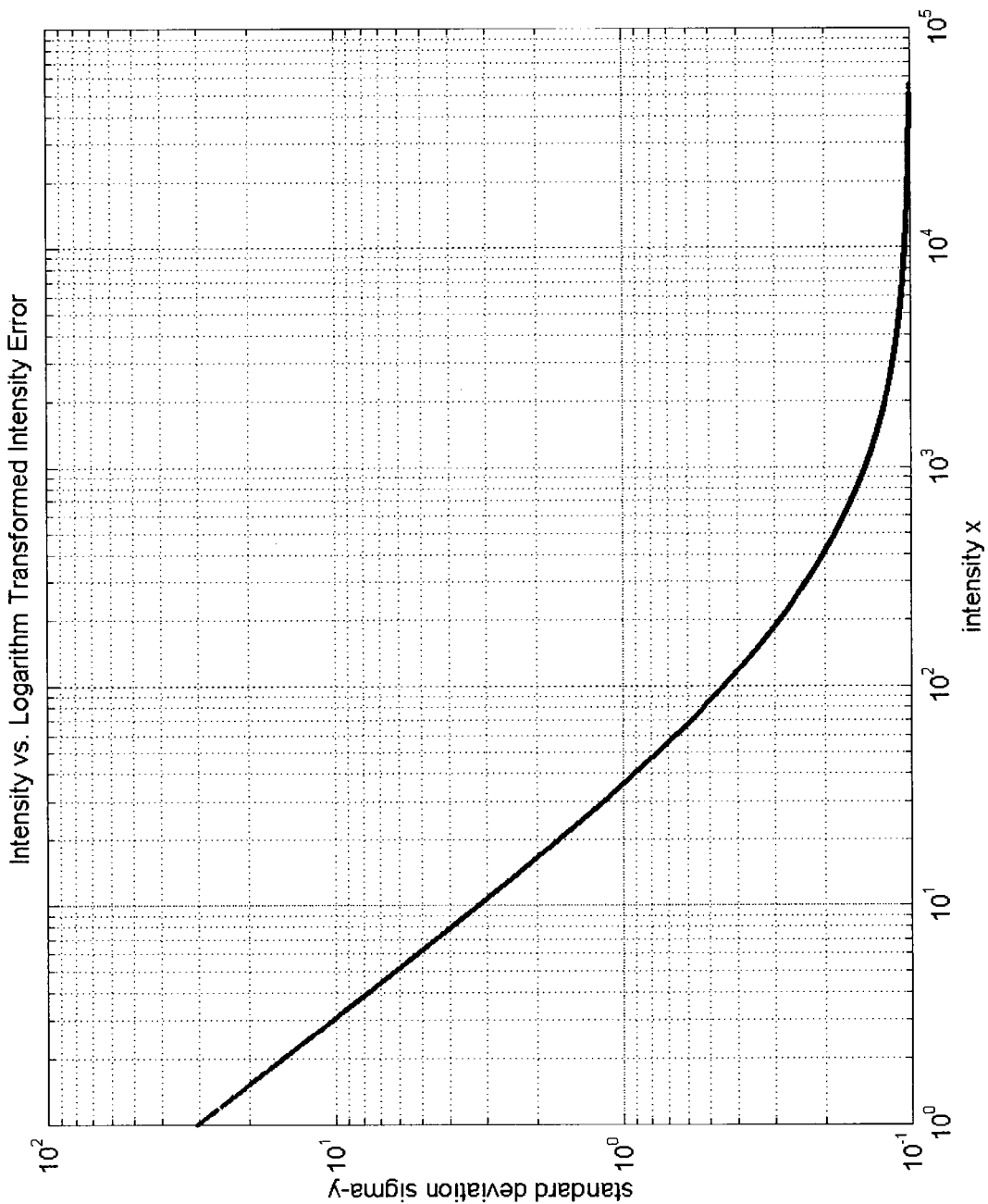
FIG. 1 shows the relationship between the intensity x and the logarithm-transformed intensity error $\sigma_y$. The error is modeled by Equation 16, in which parameters are a=0.1, b=3.16 and c=30.1.
Figure 12:
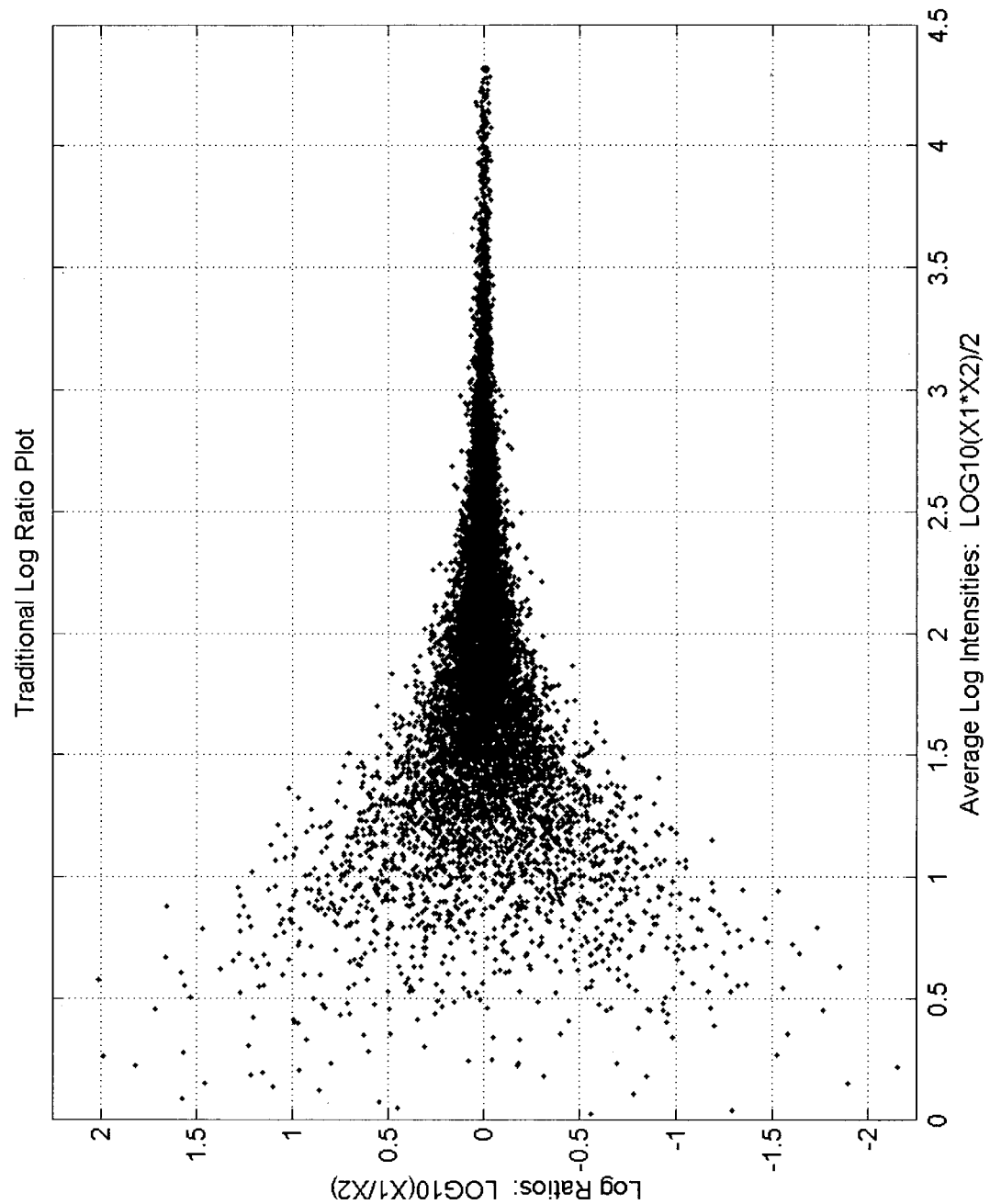

FIG. 12. An example of the traditional log-ratio plot in expression analysis. In this same-vs.-same experiment, the target intensity x1 and the control intensity x2 are the results of the same RNA sample hybridized to two different single-channel microarrays or labeled differently and then hybridized to one two-channel microarray chip. The large log ratio variation near the low average intensity side, the "fish tail", is clearly visible at the left of the plot. The noisy fish tail is the result of the ever increasing error characteristics when intensity is approaching zero, which is shown in FIG. 1, because the log ratio is the difference of two individually log-transformed intensities.

Figure 13:
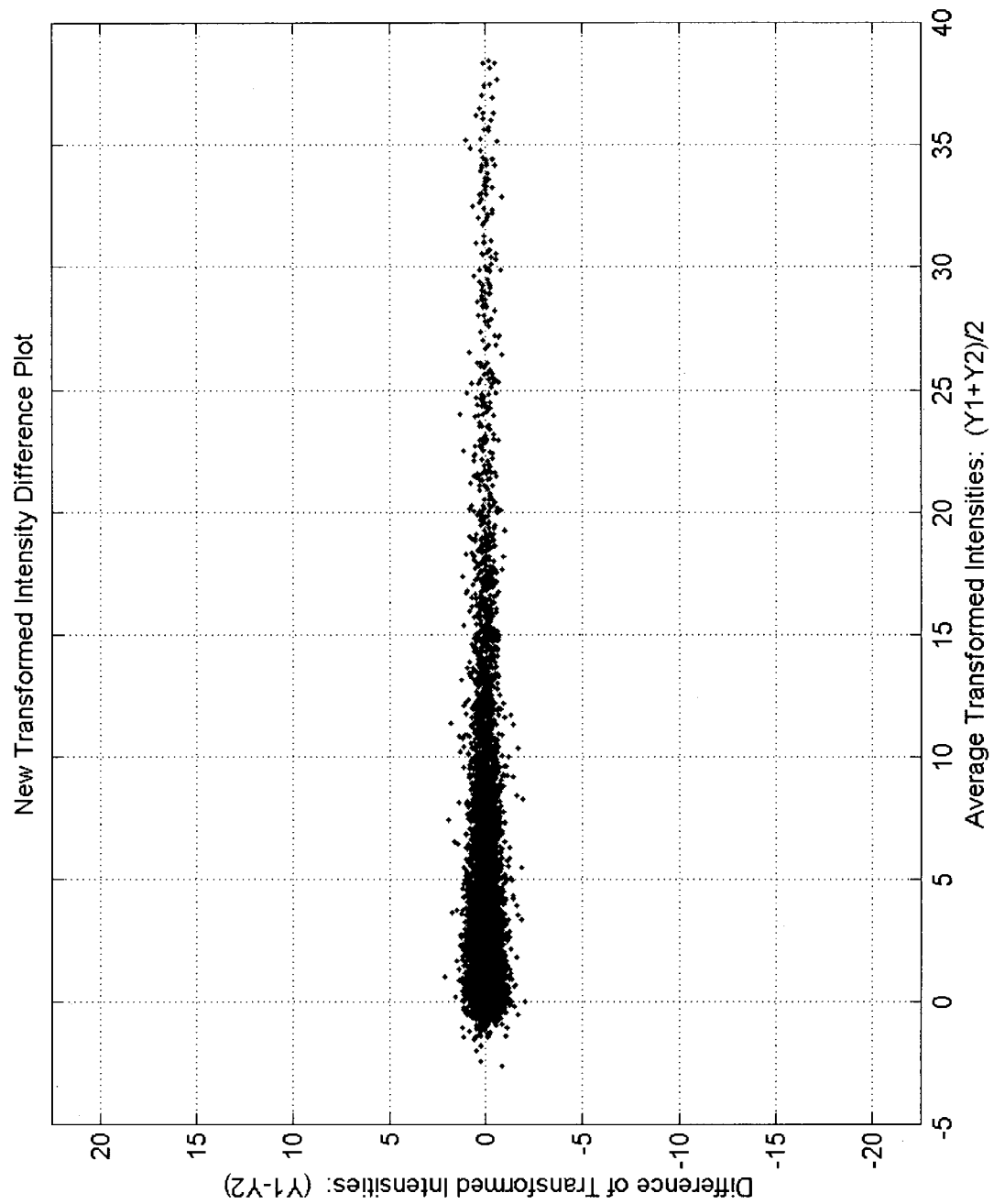

FIG. 13. An example of the difference plot in the new general-transformed intensity y domain. Microarray intensity data x used in the transformation is identical to the same-vs.-same experiment data shown in FIG. 12. There is no the noisy "fish tail" artifact in this plot. Variance of the difference is approximately a constant. The improved error characteristics in the differential expression measurement are the results of the stable and near constant error characteristics in the transformed intensities shown in FIG. 6 and FIG. 8. The low noise characteristics at the low intensity side shown in this plot make the differential expression detection (statistical test) of weakly expressed genes easier. In addition, the differential expression measurement still works and is still stable in the transformed domain even when the intensity measurement is negative.

Figure 14:
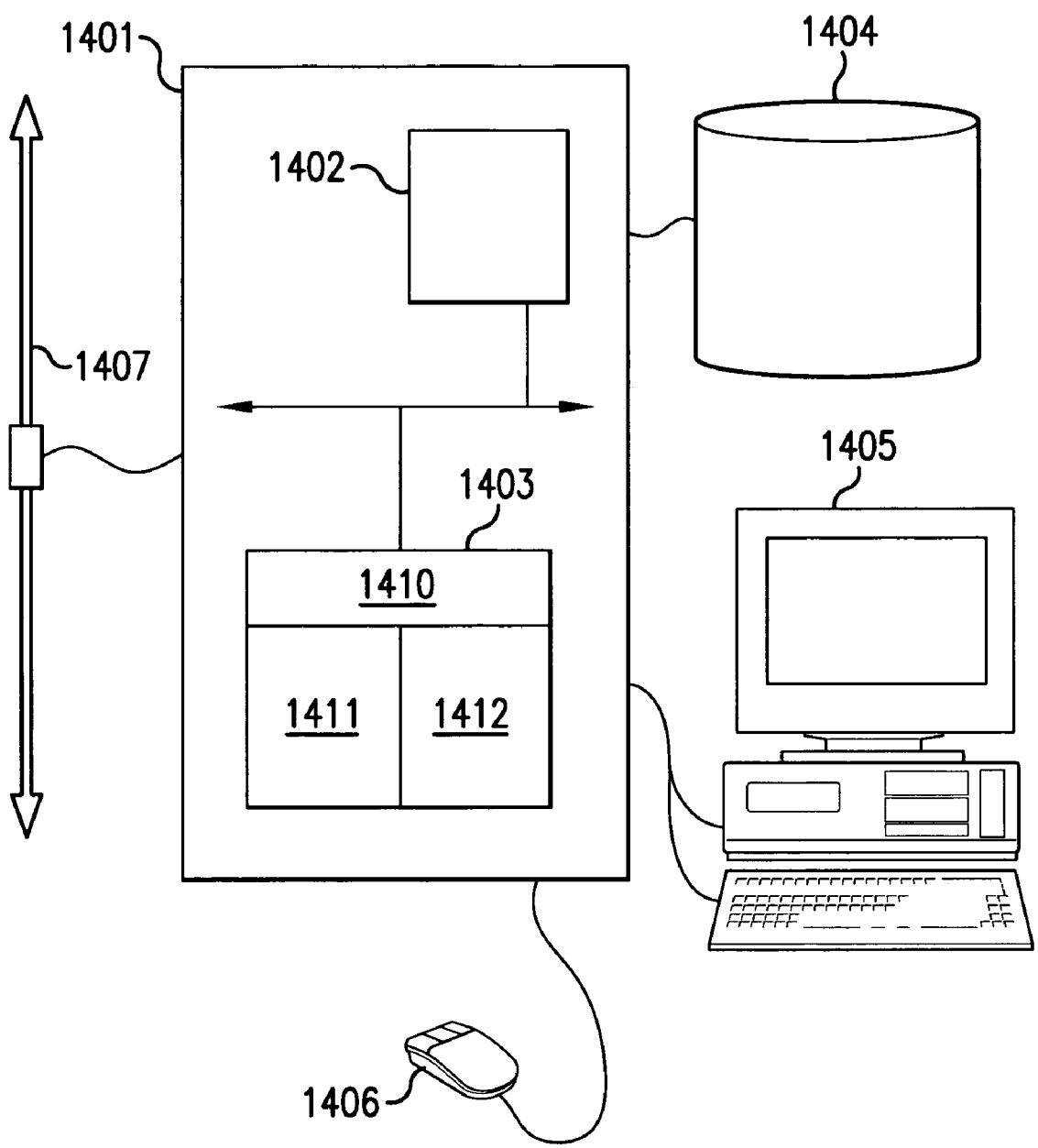

FIG. 14 illustrates an exemplary embodiment of a computer system useful for implementing the methods of this invention.

5. DETAILED DESCRIPTION OF THE INVENTION

The present invention provides methods for analyzing measurement errors in measured signals obtained in an experiment, e.g., measured intensity signals obtained in a microarray gene expression experiment. Signals from any experimental measurement can be analyzed by the methods of the present invention. For example, the measured signals can represent measurements of the abundances or activities of cellular constituents in a cell or organism; or measurements of the responses of cellular constituents in a living cell or organism to a perturbation to the living cell or organism. The methods of the invention are particularly useful for analyzing measurement errors in signals in which at least portion of the error is dependent on the magnitudes of the signals. The present inventor has discovered that transforming measured signals into a transformed domain such that the measurement errors in the transformed signals are errors in the measured signals normalized by known errors, e.g., fractional errors and Poisson errors, can greatly facilitate analysis of measurement errors in measured signals. In one embodiment of the invention, the measurement errors in measured signals are modeled by an error model, and a transformation is used to transform measured signals into a domain in which the measurement errors in the transformed signals are normalized by errors as determined from the error model. The method can be used in obtaining residue errors, i.e., errors beyond those described by the error model. In a preferred embodiment, the error model takes into account errors that are dependent on the magnitudes of the measured signals. In such an embodiment, the method can be used to transform signals into a transformed domain in which errors in the transformed signals are independent of the magnitude of the measured signals. Such transformed signals permit analysis of data using traditional statistical methods, e.g., ANOVA and regression analysis (e.g., to determine statistical significance of measured data). Magnitude-independent errors can also be used for comparing levels of measurement errors in signals of different magnitudes.

The methods of the invention are applicable to measured signals obtained by both single-channel measurement and two-channel measurement. As used herein, a "single-channel measurement" refers broadly to where measurements of cellular constituents are made on a single sample (e.g. a sample prepared from a living cell or organism having been subjected to a given condition) in a single experimental reaction, whereas a "two-channel measurement" refers to where measurements of cellular constituents are made distinguishably and concurrently on two different samples (e.g., two samples prepared from cells or organisms, each having been separately subjected to a given condition) in the same experimental reaction. The cells or organisms from which the two samples in a two-channel experiment are derived can be subjected to the same condition or different conditions. By the same experimental reaction, is meant in the same reaction mixture, i.e., by contacting with the same reagents in the same composition at the same time (e.g., using the same microarray for nucleic acid hybridization to measure mRNA, cDNA or amplified RNA; or the same antibody array to measure protein levels). In this disclosure, a measurement in a "same-vs.-same" experiment is often referred to. As used herein, such a measurement refers to either a two-channel measurement performed in an experiment in which the two samples are derived from cells or organism having been subjected to the same condition or a measurement obtained in two single-channel measurements performed separately with two samples which are derived from cells or organisms having been subjected to the same condition.

In this disclosure, for simplicity reasons, the invention is often described in terms of using measured signals obtained from a microarray experiment. It will be clear to a person of ordinary skill in the art that the methods of the present invention are equally applicable to signals measured in many other kinds of experiments, e.g., signals measured in a protein array experiment or signals measured in a 2D protein gel experiment.

5.1. Biological State and Expression Profile

The state of a cell or other biological sample is represented by cellular constituents (any measurable biological variables) as defined in Section 5.1.1, infra. Those cellular constituents vary in response to perturbations, or under different conditions. The measured signals can be measurements of such cellular constituents or measurements of responses of cellular constituents.

5.1.1 Biological State

As used herein, the term "biological sample" is broadly defined to include any cell, tissue, organ or multicellular organism. A biological sample can be derived, for example, from cell or tissue cultures in vitro. Alternatively, a biological sample can be derived from a living organism or from a population of single cell organisms. In preferred embodiments, the biological sample comprises a living cell or organism.

The state of a biological sample can be measured by the content, activities or structures of its cellular constituents. The state of a biological sample, as used herein, is taken from the state of a collection of cellular constituents, which are sufficient to characterize the cell or organism for an intended purpose including, but not limited to characterizing the effects of a drug or other perturbation. The term "cellular constituent" is also broadly defined in this disclosure to encompass any kind of measurable biological variable. The measurements and/or observations made on the state of these constituents can be of their abundances (i.e., amounts or concentrations in a biological sample) e.g., of mRNA or proteins, or their activities, or their states of modification (e.g., phosphorylation), or other measurements relevant to the biology of a biological sample. In various embodiments, this invention includes making such measurements and/or observations on different collections of cellular constituents. These different collections of cellular constituents are also called herein aspects of the biological state of a biological sample.

One aspect of the biological state of a biological sample (e.g., a cell or cell culture) usefully measured in the present invention is its transcriptional state. In fact, the transcriptional state is the currently preferred aspect of the biological state measured in this invention. The transcriptional state of a biological sample includes the identities and abundances of the constituent RNA species, especially mRNAs, in the cell under a given set of conditions. Preferably, a substantial fraction of all constituent RNA species in the biological sample are measured, but at least a sufficient fraction is measured to characterize the action of a drug or other perturbation of interest. The transcriptional state of a biological sample can be conveniently determined by, e.g., measuring cDNA abundances by any of several existing gene expression technologies. One particularly preferred embodiment of the invention employs DNA arrays for measuring mRNA or transcript level of a large number of genes. The other preferred embodiment of the invention employs DNA arrays for measuring expression levels of a large number of genes or exons in the genome of an organism.

Another aspect of the biological state of a biological sample usefully measured in the present invention is its translational state. The translational state of a biological sample includes the identities and abundances of the constituent protein species in the biological sample under a given set of conditions. Preferably, a substantial fraction of all constituent protein species in the biological sample is measured, but at least a sufficient fraction is measured to characterize the action of a drug of interest. As is known to those of skill in the art, the transcriptional state is often representative of the translational state.

Other aspects of the biological state of a biological sample are also of use in this invention. For example, the activity state of a biological sample, as that term is used herein, includes the activities of the constituent protein species (and also optionally catalytically active nucleic acid species) in the biological sample under a given set of conditions. As is known to those of skill in the art, the translational state is often representative of the activity state.

This invention is also adaptable, where relevant, to "mixed" aspects of the biological state of a biological sample in which measurements of different aspects of the biological state of a biological sample are combined. For example, in one mixed aspect, the abundances of certain RNA species and of certain protein species, are combined with measurements of the activities of certain other protein species. Further, it will be appreciated from the following that this invention is also adaptable to other aspects of the biological state of the biological sample that are measurable.

The biological state of a biological sample (e.g., a cell or cell culture) is represented by a profile of some number of cellular constituents. Such a profile of cellular constituents can be represented by the vector S, $$S=[S_1, \ldots S_i, \ldots S_k] \quad (1)$$

where $S_i$ is the level of the i'th cellular constituent, for example, the transcript level of gene i, or alternatively, the abundance or activity level of protein i.

In some embodiments, cellular constituents are measured as continuous variables. For example, transcriptional rates are typically measured as number of molecules synthesized per unit of time. Transcriptional rate may also be measured as percentage of a control rate. However, in some other embodiments, cellular constituents may be measured as categorical variables. For example, transcriptional rates may be measured as either "on" or "off", where the value "on" indicates a transcriptional rate above a predetermined threshold and value "off" indicates a transcriptional rate below that threshold.

5.1.2 Biological Responses and Expression Profiles

The responses of a biological sample to a perturbation, i.e., under a condition, such as the application of a drug, can be measured by observing the changes in the biological state of the biological sample. For example, the responses of a biological sample can be responses of a living cell or organism to a perturbation, e.g., application of a drug, a genetic mutation, an environmental change, and so on, to the living cell or organism. A response profile is a collection of changes of cellular constituents. In the present invention, the response profile of a biological sample (e.g., a cell or cell culture) to the perturbation m is defined as the vector $v^{(m)}$:

$$v^{(m)}=[v_1^{(m)}, \ldots v_i^{(m)}, \ldots v_k^{(m)}] \quad (2)$$

Where $v_i^m$ is the amplitude of response of cellular constituent i under the perturbation m. In some particularly preferred embodiments of this invention, the biological response to the application of a drug, a drug candidate or any other perturbation, is measured by the induced change in the transcript level of at least 2 genes, preferably more than 10 genes, more preferably more than 100 genes and most preferably more than 1,000 genes. In another preferred embodiment of the invention, the biological response to the application of a drug, a drug candidate or any other perturbation, is measured by the induced change in the expression levels of a plurality of exons in at least 2 genes, preferably more than 10 genes, more preferably more than 100 genes and most preferably more than 1,000 genes.

In some embodiments of the invention, the response is simply the difference between biological variables before and after perturbation. In some preferred embodiments, the response is defined as the ratio of cellular constituents before and after a perturbation is applied.

In some preferred embodiments, $v_i^m$ is set to zero if the response of gene i is below some threshold amplitude or confidence level determined from knowledge of the measurement error behavior. In such embodiments, those cellular constituents whose measured responses are lower than the threshold are given the response value of zero, whereas those cellular constituents whose measured responses are greater than the threshold retain their measured response values. This truncation of the response vector is a good strategy when most of the smaller responses are expected to be greatly dominated by measurement error. After the truncation, the response vector $v^{(m)}$ also approximates a 'matched detector' (see, e.g., Van Trees, 1968, *Detection, Estimation and Modulation Theory Vol. I*, Wiley & Sons) for the existence of similar perturbations. It is apparent to those skilled in the art that the truncation levels can be set based upon the purpose of detection and the measurement errors. For example, in some embodiments, genes whose transcript level changes are lower than two fold or more preferably four fold are given the value of zero.

In some preferred embodiments, perturbations are applied at several levels of strength. For example, different amounts of a drug may be applied to a biological sample to observe its response. In such embodiments, the perturbation responses may be interpolated by approximating each by a single parameterized "model" function of the perturbation strength u. An exemplary model function appropriate for approximating transcriptional state data is the Hill function, which has adjustable parameters a, $u_0$, and n.

$$H(u) = \frac{a(u/u_0)^n}{1 + (u/u_0)^n} \quad (3)$$

The adjustable parameters are selected independently for each cellular constituent of the perturbation response. Preferably, the adjustable parameters are selected for each cellular constituent so that the sum of the squares of the differences between the model function (e.g., the Hill function, Equation 3) and the corresponding experimental data at each perturbation strength is minimized. This preferable parameter adjustment method is well known in the art as a least squares fit. Other possible model functions are based on polynomial fitting, for example by various known classes of polynomials. More detailed description of model fitting and biological response has been disclosed in Friend and Stoughton, Methods of Determining Protein Activity Levels Using Gene Expression Profiles, PCT publication WO 99/59037, which is incorporated herein by reference in its entirety for all purposes.

5.2. Measurement Errors in Measured Signals and Error Models

Measured signals obtained in a microarray experiment often contain errors due both to the inherent stochastic nature of gene expression and to measurement errors from various external sources. The many sources of measurement error that may occur in a measured signal include those that fall into three categories—additive error, multiplicative error, and Poisson error. The signal magnitude-independent or intensity-independent additive error includes errors resulting from, e.g., background fluctuation, or spot-to-spot variations in signal intensity among negative control spots, etc. The signal magnitude-dependent or intensity-dependent multiplicative error, which is assumed to be directly proportional to the signal intensity, includes errors resulting from, e.g., the scatter observed for ratios that should be unity. The multiplicative error is also termed fractional error. The third type of error is a result of variation in number of available binding sites in a spot. This type of error depends on the square-root of the signal magnitude, e.g., measured intensity. It is also called the Poisson error, because it is believed that the number of binding sites on a microarray spot follows a Poisson distribution, and has a variance which is proportional to the average number of binding sites.

5.2.1. Error Models

Errors in measured signals can be described by error models (see, e.g., Supplementary material to Roberts et al, 2000, Science, 287:873-880; and Rocke et al., 2001, J. Computational Biology 8:557-569). In preferred embodiments, an error model (see, e.g., Supplementary material to Roberts et al, 2000, Science, 287:873-880; and Rocke et al., 2001, J. Computational Biology 8:557-569) contains two or three error terms to describe the dominant error sources. In a two-term error model, a first error term is used to describe the low-level additive error which comes from, e.g., the background of the array chip. Since this additive error has a constant variance, in this disclosure, it is also called the constant error. The constant error is independent from the hybridization levels of individual spots on a microarray. It may come from the combination of the scanner electronics noise and/or fluorescence due to nonspecific binding of fluorescence molecules to the surface of the microarray. In one embodiment, this constant additive error is taken to have a normal distribution with a mean bkg and a standard deviation $\sigma_{bkg}$. After background level subtraction, which is typically applied in microarray data processing, the additive mean bkg becomes zero. In this disclosure, it is often assumed that the background intensity offset has been corrected. An ordinary skilled artisan in the art will appreciate that in cases where the background mean is not corrected, the methods of the invention can be used with an additional step of making such a correction.

The second error source is the multiplicative error that is the combined result of the speckle noise inherent in the coherent laser scanner and the fluorescence dye related noise. The multiplicative error is also called fractional error because its level is directly proportional to the magnitude of the measured signal, e.g., the measured intensity level. It is the dominant error source at high intensity levels. In one embodiment in which the measured signal is obtained from a microarray experiment, the standard deviation of the fractional error in the k'th spot can be approximated as $$\sigma_{frac}(k) \approx a \cdot x(k) \quad (4)$$

where x(k) is the measured intensity in the k'th spot. The constant a in Equation 4 is termed fractional error coefficient, and describes the proportion of the fractional error to the intensity of the measured signal. In one embodiment, the constant has a value in the range of 0.1 to 0.2. This constant may vary depending on the particular microarray technology used for obtaining the measured signal and/or the particular hybridization protocol used in the measurement. In one embodiment, parameter a is determined during the error building phase by measuring the variance of the log ratio near the high intensity side in a same-vs.-same ratio experiment where the intensities in the ratio numerator and denominator come from the same sample and treatment. At high intensities, the variance of log ratio $x_1$ over $x_2$ relates to parameter a:

$$Var\{\ln(x_1/x_2)\} \approx \frac{(a \cdot x_1)^2}{x_1^2} + \frac{(a \cdot x_2)^2}{x_2^2} = 2 \cdot a^2 \quad (5)$$

when $x_1$ and $X_2 >> \sigma_{bkg}$. In one embodiment, $x_1$ and $x_2$ are at least 4, 10, 50, 100, or 200 times $\sigma_{bkg}$.

In a two-term error model, the measurement error in a measured signal, e.g., measured intensity, x(k) can be defined as $$\sigma_x(k) = \sqrt{\sigma_{bkg}(k)^2 + \sigma_{frac}(k)^2} \approx \sqrt{\sigma_{bkg}(k)^2 + a^2 \cdot x(k)^2} \quad (6)$$

In a preferred embodiment of the invention, we assume the background noise variances in Equation 6 are slightly different in different microarray spots or regions of a microarray chip. In one embodiment, the difference is less than 20%, 10%, 5%, or 1%.

In a three-term error model, an extra square-root term is included to describe measurement errors originated from variation in the number of available binding sites in a microarray spot. This term is also called the Poisson term. In one embodiment, without knowledge of actual number of binding sites in a microarray spot, the measured intensity is used to provide an estimate of the average number of binding sites. In such an embodiment, the Poisson error can be approximated as $$\sigma_{Poisson}(k) \approx b \cdot \sqrt{x(k)} \qquad (7)$$

where parameter b is an overall proportional factor, termed Poisson error coefficient. In a three-term error model, the measurement error in a measured signal, e.g., a measured fluorescence intensity, x(k) can be defined as $$\sigma_x(k) = \sqrt{\sigma_{bkg}(k)^2 + \sigma_{Poisson}(k)^2 + \sigma_{frac}(k)^2} \qquad (8)$$
$$\approx \sqrt{\sigma_{bkg}(k)^2 + b^2 \cdot x(k) + a^2 \cdot x(k)^2}$$

In a preferred embodiment, during error model development, when $\sigma_{bkg}$ and parameter a have been determined, parameter b in Equation 8 is determined by measuring the intensity variance in the middle intensity ranges of the same-vs.-same experiments. In one embodiment, the intensity variance is measured in the 25 to 75 percentile range, 35 to 65 percentile range, or 45 to 50 percentile range for determination of b.

In a preferred embodiment, after the error model development phase, parameters a and b are fixed for an error model under a given microarray technology and experiment protocol. The background noise $\sigma_{bkg}$ can be estimated for each particular microarray experiment. In another preferred embodiment, when a set of replicate experiments are carried out, the background noise $\sigma_{bkg}$ for the set can be obtained by averaging the background noise estimated for each of the replicate experiments.

The two-term error model as described by Equation 6 can been seen as a simplified version of the three-term error model described by Equation 8 by setting the Poisson parameter b to zero. In this disclosure, Equation 8 is used as the general mathematical description of error models. It will be apparent to an ordinarily skilled artisan that any results obtained based on Equation 8 are also applicable to a two-term error model by setting the Poisson parameter b to zero.

5.2.2. Intensity Transformations

Many data processing and statistical analysis methods are applicable to measured data in which the variance of measurement errors is constant. Preferably, for use in such methods the variance of measurement errors of such data does not depend on the magnitudes of the measurements over a range of measurement magnitudes. For example, in the commonly used analysis of variance (ANOVA) method, the variables under investigation preferably have a constant variance. In another example, many data regression and parametric or non-parametric modeling methods used in data normalization and detrending to remove the intensity dependent non-linearity have the underlying assumption that the data are not heteroskedastic (i.e., do not have a changing variance).

It is very clear from Equation 8 that microarray intensity measurements do not meet the constant-variance requirement. There are different measurement errors (or variances) in different intensities. The intensity error is a function of intensity itself. To overcome this problem, a function $f()$ is needed to transform measured signals, e.g. the intensity data, x to a new domain y in which the variance becomes a constant.

All analysis and data processing can then be carried out in the transformed domain. In a preferred embodiment, such a transformation is described as $$y(k)=f(x(k)), \text{ for all } x \text{ and} \qquad (9)$$

$$\sigma_y(k) \approx C, \text{ for all } x \text{ where } C \text{ is a constant.} \qquad (10)$$

Preferably the transformation works for both positive and negative (e.g, negative signals obtained after background subtraction) x. More preferably the transformation meets the following additional constraints:
  (i) Monotonic: If $x(k_1) > x(k_2)$, we should have $y(k_1) > y(k_2)$ for all x;
  (ii) Zero intercept: $f(0)=0$; and
  (iii) Smooth: The first and the second derivatives of the function f should be continuous functions.

Still more preferably, an inverse transformation function g exists so that the transformed signals in the transformed domain can be transformed back to the original domain. The inverse transformation does the following operation:

$$x(k)=g(y(k)), \text{ for all } y \qquad (11)$$

Preferably, the inverse transformation function g meets above four constraints as well. In one embodiment, the error in the inversely transformed intensity can be determined when the first derivative $f'()$ of the forward transformation function $f$ is available:

$$\sigma_x(k) \approx \frac{\sigma_y(k)}{df(x(k))/dx(k)} = \frac{\sigma_y(k)}{f'(x(k))} \qquad (12)$$

It is most preferable that the forward transformation function $f$, its first derivative $f'$, and the inverse transformation function g are all in analytical closed-forms.

In the following two subsections, certain prior art transformations and their limitations are discussed, and it is shown that such prior art transformations do not meet the above constraints.

5.2.2.1. Logarithmic Transformation

A transformation function commonly used in the prior art is a logarithm:

$$y(k)=f(x(k))=ln(x(k)), \text{ for } x>0 \qquad (13)$$

In Equation 8, when intensity x is very high, the fractional error is the dominant error source. In this case, the standard deviation of y is approximately a constant:

$$\sigma_y(k) \approx \sigma_x(k) \cdot f'(x(k)) \approx \frac{a \cdot x(k)}{x(k)} = a, \text{ when } x \text{ is very large} \qquad (14)$$

But when intensity x is low, the standard deviation of y is inversely proportional to x, and is approaching infinity:

$$\sigma_y(k) \approx \sigma_x(k) \cdot f'(x(k)) \approx \frac{\sigma_{bkg}(k)}{x(k)}, \text{ when } x \text{ is very small} \qquad (15)$$

FIG. 1 is an exemplary plot of the relationship between the intensity x and the transformed error $\sigma_y$. The original intensity error $\sigma_x$ is modeled by a simplified three-term error model in Equation 16:

$$\sigma_x(k) \approx \sqrt{c^2 + b^2 \cdot x(k) + a^2 \cdot x(k)^2} \qquad (16)$$

where constant c=Mean{$\sigma_{bkg}$ (k)}. In this example, a=0.1, b=3.16 and c=30.1, which are real parameters in a particular error model for a typical microarray chip. In addition, the logarithmic transformation does not work when x is equal to or less than zero.

It is clear that the logarithm transformation does not meet the requirements listed supra.

5.2.2.2. Piecewise Hybrid Transformation

To overcome certain of the limitations of the logarithmic transformation, a piecewise hybrid transformation has been used in the prior art for signal and error conversion (see, e.g., D. Holder, et al, "Quantitation of Gene Expression for High-Density Oligonucleotide Arrays: A SAFER Approach", presented in Genelogic Workshop on Low Level Analysis of Affymetrix Genechip® data, Nov. 19, 2001, Bethesda, Md., http://oz.berkeley.edu/users/terry/zarray/Affy/GL_Workshop/Holder.ppt). This hybrid transformation uses a linear function at the low intensity side and a logarithm function for high intensities. An arbitrary parameter c' defines the boundary between the linear and the logarithmic functions. Equation 17 is the mathematical definition of the hybrid transformation function.

$$y(k) = f(x(k)) = x(k), \text{ for } 0 \leq x(k) < c'$$

$$y(k) = f(x(k)) = c' \cdot ln(x(k)/c') + c', \text{ for } x(k) \geq c'$$

$$y(k) = f(x(k)) = 0, \text{ for } x(k) < 0 \qquad (17)$$

In one embodiment, parameter c' in Equation 17 is chosen to be 20. Errors of the hybrid-transformed intensities can be estimated as $$\sigma_y(k) \approx \sigma_x(k) \cdot f'(x(k)) = \sigma_x(k), \text{ for } 0 \leq x(k) < c'$$

$$\sigma_y(k) \approx \sigma_x(k) \cdot f'(x(k)) = c' \cdot \sigma_x(k)/x(k), \text{ for } x(k) \geq c' \qquad (18)$$

Figure 2:
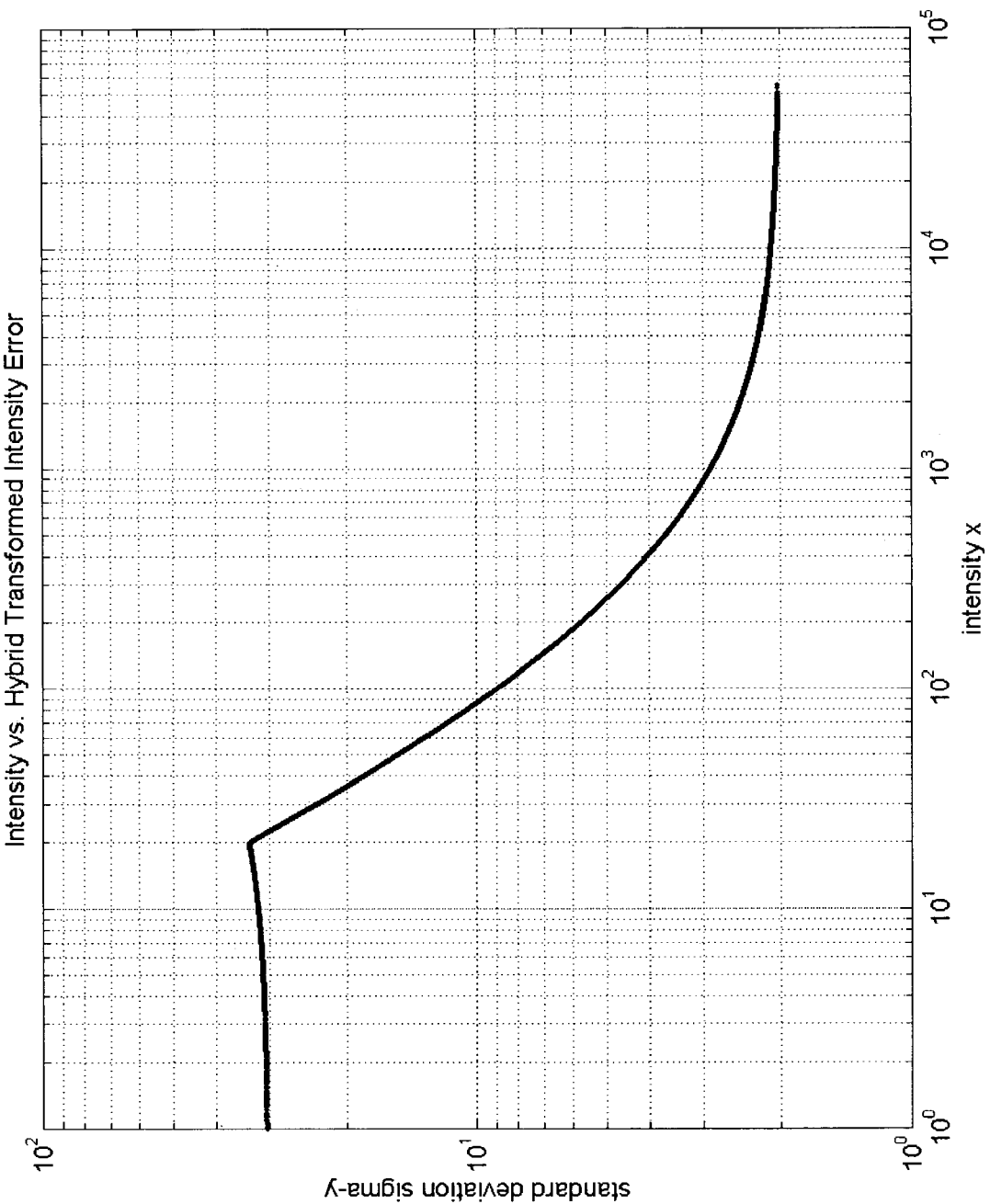
FIG. 2 shows the relationship between the intensity x and the hybrid-transformed intensity error $\sigma_y$. The error is modeled by Equation 16, in which parameters are a=0.1, b=3.16 and c=30.1.

FIG. 2 is an exemplary plot of the relationship between measured intensity x and transformed error $\sigma_y$. The original intensity error $\sigma_x$ is also modeled by a three-term error model in Equation 16. Comparing to the logarithmic transformation in FIG. 1, the hybrid transformation in FIG. 2 clearly offers improvements in controlling the error expansion at the low intensity side. However, the measurement error, $\sigma_y$, of the hybrid-transformed intensity is still far from a constant. The range of the transformed error spans more than fifteen folds.

In addition, the piecewise hybrid transformation does not meet Constraint (iii), supra. Even though its first derivative function is continuous at the boundary point c', its second derivative function is not. Such a non-smooth transformation function will distort the intensity distribution in real microarray data. An example of the distortion is discussed in Example Section 6.

5.3. Methods of Analyzing Errors in Measured Signals

The invention provides methods of analyzing errors in measured signals. In one aspect of the invention, a transformation is provided and used to transform measured signals obtained in an experiment to a transformed domain such that the measurement errors in transformed signals are equal to the measurement errors in the measured signals normalized by errors determined based on an error model. As used in this disclosure, such an measurement error, i.e., a measurement error which equals the measurement error in the measured signal normalized by an error determined based on an error model, is also referred to as a normalized error. Any suitable error model can be used in the invention. In a preferred embodiment, the error model is a two-term or a three-term error model described in Section 5.2.1. In a particularly preferred embodiment, the variance of the transformed signals in the transformed domain is close to a constant. More preferably, the transformation meets all requirements discussed in Section 5.2.2. The basic concept of the new transformation method is to apply an error model to normalize errors in real measurements, e.g., standard deviations in measured signals, such that the normalized errors are close to a constant. Then a transformation function $f(\ )$ is found by the integration of the normalization function. The methods are applicable to any set of measured signals whose errors can be described by a particular error model.

In a specific embodiment, the real measurement standard deviation $\Delta x$ is for the positive intensity x>0. The real standard deviation $\Delta x$ is usually known before the transformation. An error model in Equation 16 provides $\sigma_x$ that is an estimate of the real standard deviation $\Delta x$ for different intensities. In one embodiment, $\Delta x$ is an error determined by the experiment. In another embodiment, $\Delta x$ is calculated using an error model of the experiment. In a preferred embodiment, $\Delta x$ is chosen to be the larger of an experimentally determined error or an error model-calculated error. Assuming the transformed standard deviation is $\Delta y$, the following approximation relates the two errors with the first derivative function of the transformation:

$$f'(x) = \frac{dy}{dx} \approx \frac{\Delta y}{\Delta x} \qquad (19)$$

If the equation is rearranged, one obtains $$\Delta y \approx \Delta x \cdot f'(x) \qquad (20)$$

Because Equation 16 is an approximation of $\Delta x$, if a normalization function y' is defined as follows:

$$y' = f'(x) = \frac{1}{\sqrt{c^2 + b^2 \cdot x + a^2 \cdot x^2}}, \text{ for } x > 0, \qquad (21)$$

where a, b, and c are defined as in Section 5.2, one can expect that the variance of y is close to a constant.

Equation 21 provides an analytical form of the first derivative function of the desired transformation. To obtain the transformation function itself, both sides of Equation 21 are integrated:

$$y = f(x) = \int f'(x) \cdot dx = \int \frac{dx}{\sqrt{c^2 + b^2 \cdot x + a^2 \cdot x^2}}, \text{ for } x > 0 \qquad (22)$$

Fortunately, the integral in Equation 22 does have an analytical solution. By using a symbolic-solution software, such as Mathematica, or using an integral table, the solution is obtained as $$y = f(x) = \frac{\ln\left(\frac{b^2 + 2 \cdot a^2 \cdot x}{a} + 2 \cdot \sqrt{c^2 + b^2 \cdot x + a^2 \cdot x^2}\right)}{a} + d, \text{ for } x > 0 \quad (23)$$

Applying the zero intercept constraint (ii) in Section 5.2.2, i.e., y=0 when x=0, the constant d in Equation 23 is found to be $$d = \frac{-\ln\left(\frac{b^2}{a} + 2 \cdot c\right)}{a} \quad (24)$$

As indicated in Equation 11 in Section 5.2.2, preferably one finds the inverse transformation function g(y) so that the transformed intensity y can be converted back to the original x scale whenever necessary. By using linear algebra or a symbolic-solution software, such as Maple, one finds $$x = g(y) = \frac{-(4 \cdot a^2 \cdot c^2 - a^2 \cdot e^{2a \cdot (y-d)} + 2 \cdot a \cdot b^2 \cdot e^{a \cdot (y-d)} - b^4)}{4 \cdot a^3 \cdot e^{a \cdot (y-d)}}, \quad (25)$$

for y > 0

To complete the forward and the inverse transformation pair for both intensity and its error, the standard deviation of the inversely transformed intensity can be estimated by using Equation 12.

In a specific embodiment, the transformation function can be further defined to be symmetric to zero for all x. When x<0, the absolute value |x| is used to replace x in the forward transformation in Equation 23 and to give a negative sign to the result y. In the inverse transformation in Equation 25, when y<0, the absolute value |y| is used to replace y and to give a negative sign to the result x.

Figure 3:
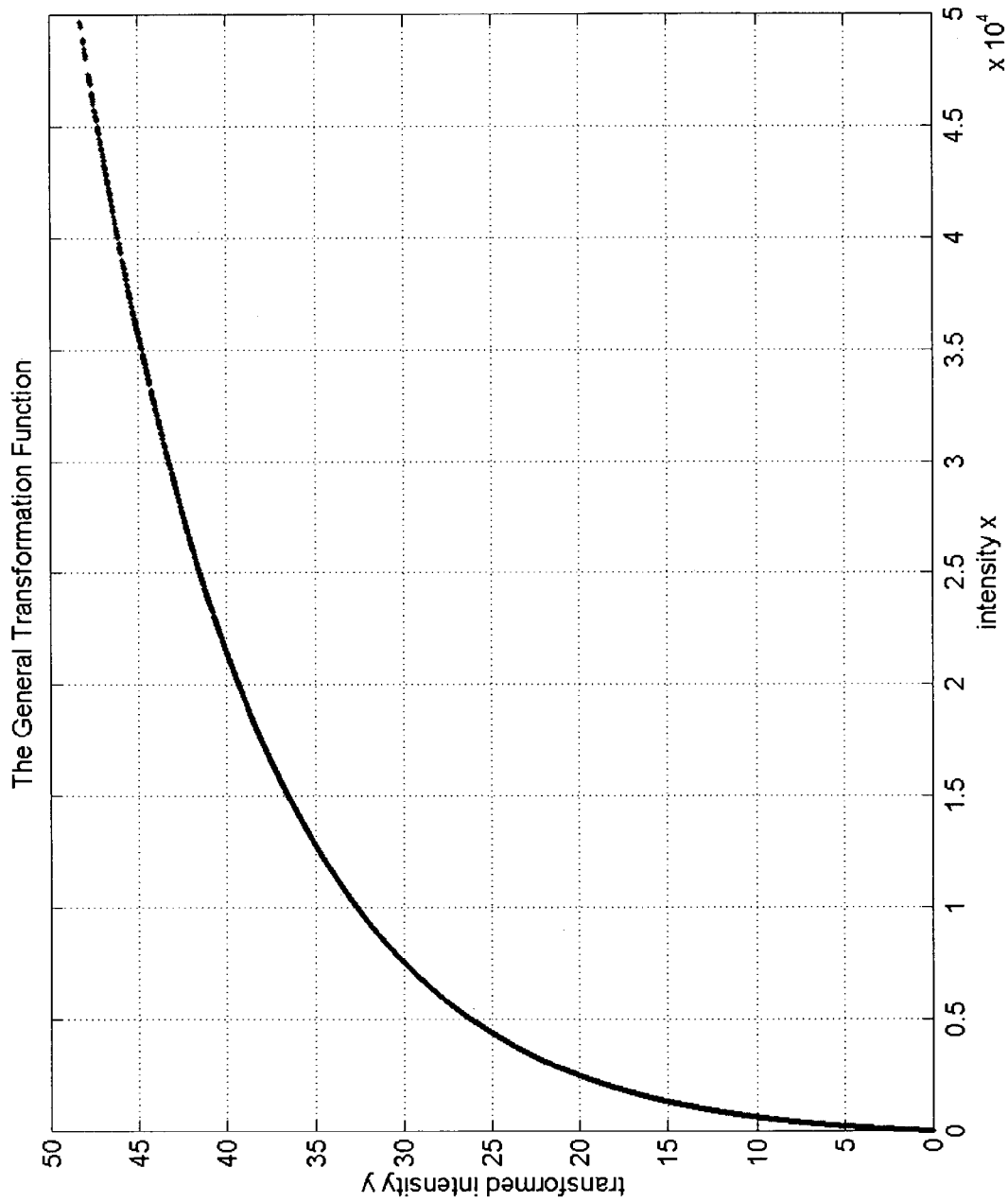
FIG. 3 shows the relationship between the intensity x and the transformed intensity y in the proposed general transformation functions. Parameters in the transformation are a=0.1, b=3.16, c=30.1 and d=−50.8.

FIG. 3 shows the x and y relationship under the obtained transformation as described by Equation 23 and Equation 25. Under the forward transformation, the estimated transformed error $\sigma_y$ is one over all intensity ranges of x or y, so that constant C=1 in Equation 10. The transformation also meets all other requirements and constraints stated in Section 5.2.2. In addition, the transformation has several other interesting properties:

$$y = f(x) \approx \frac{\ln(4 \cdot a \cdot x)}{a}, \text{ when } x \text{ is very large} \quad (26)$$

$$y' = f'(x) \approx \frac{1}{c}, \text{ when } |x| \text{ is very small} \quad (27)$$

The transformation described in this section is applicable to any measured signals in which the errors can be described by a three-term error model. In preferred embodiments, the measured signals are measured in a microarray gene expression experiment. In other preferred embodiments, the measured signals are measured in a protein array experiment or a 2D gel protein experiment.

In one preferred embodiment, the measured signals are signals obtained in an microarray experiment in which two spots or probes on a microarray are used for obtaining each measured signal, one comprising the targeted nucleotide sequence, i.e., the target probe (TP), e.g., a perfect-match probe, and the other comprising a reference sequence, i.e., a reference probe (RP), e.g., a mutated mismatch probe. The RP probe is used as a negative control, e.g., to remove undesired effects from non-specific hybridization. In one embodiment, the measured signal obtained in such a manner is defined as the difference between the intensities of the TP and RP, $x_{TP} - x_{RP}$. In such an embodiment, the fractional error, the Poisson error, and the background constant error $\sigma_{bkg}$ are described respectively according to equations $$\sigma_{frac}(k) \approx a \cdot x(k) = a \cdot \sqrt{x_{TP}(k)^2 + x_{RP}(k)^2} \quad (28)$$

$$\sigma_{Poisson}(k) \approx b \cdot \sqrt{x(k)} = b \cdot (x_{TP}(k)^2 + x_{RP}(k)^2)^{1/4} \quad (29)$$

$$\sigma_{bkg}(k) = \sqrt{\sigma_{bkg\_TP}(k)^2 + \sigma_{bkg\_RP}(k)^2} \quad (30)$$

The transformation described in this section remains applicable if we use Equations 28-30 for the fractional error, the Poisson error and the background constant error, respectively. In one embodiment, the TP probe is a perfect-match probe (PM), and the RP probe is a mismatch probe (MM) (see, e.g., Lockhart et al., 1996, *Nature Biotechnology* 14:1675). In another embodiment, the RP probe is a reverse probe of the TP probe, i.e., the RP probe has a sequence that is the reverse complement of the TP probe (see, Shoemaker et al., U.S. patent application Ser. No. 09/781,814, filed on Feb. 12, 2001; and Shoemaker et al., U.S. patent application Ser. No. 09/724,538, filed on Nov. 28, 2000).

In one embodiment, the transformation is used to determine the residue errors in measured signals. As used in this disclosure, a residue error in a measured signal refers to an error which is beyond those errors described by an error model for the experiment in which the measured signal is obtained. In this embodiment of the invention, a measured signal is first transformed into a transformed signal y by a method comprising using a transformation of this section. A normalized error is then determined by determining an error in the transformed signal y. The residue error is then determined by subtracting 1 from the normalized error.

It will be apparent to one skilled in the art that although the transformations as described by equations 23 and 25 are preferably carried out using parameters a, b, and c chosen based on a three-term error model, the transformations as described by equations 23 and 25 can also be used by replacing parameters a, b, and c with other parameters. Embodiments using such parameters are also encompassed by the present invention.

5.4. Methods of Processing and Analyzing Measured Signals

The present invention also provides methods of processing and analyzing measured signals using signals transformed by the methods described in Section 5.3. Statistical data processing and analysis methods known in the art can be used in conjunction with the transformed signals.

5.4.1. Methods of Analyzing Measured Signals

In one embodiment, the invention provides a method of analyzing measured signals based on transformed signals obtained by the methods of Section 5.3. Most statistical tests, such as analysis of variance (ANOVA) and t-test, require that the variance of the data being a constant. In preferred embodiments of the invention, the transformed signals have this property, i.e., statistical tests in such a transformed domain satisfy the underlying requirement of constant variance. The test results in the transformed domain are more accurate than results obtained in situations where no transformation is used or other non-constant-variance transformation methods are used.

In many statistical tests, the measurement error is required to be independent from the measurement quantity (constant measurement variance). Analysis of Variance (ANOVA) is an example (see, e.g., Statistics For Experimenters, Box, Hunter and Hunter, John Wiley and Sons, 1978; Siegel et al., Nonparametric statistics for the behavioural sciences, McGraw Hill, $2^{nd}$ edition, 1998; Conover, Practical Nonparametric Statistics, John Wiley and Sons, $3^{rd}$ edition, 1998; Altman, Practical Statistics for Medical Research, CRC Press, 1991; Berry, Statistical Methods in Medical Research, Blackwell Science, Inc., 2001). ANOVA is a method for detecting whether there are statistical differences among the mean of different measurement groups. As an example, a measurement group may contain a set of gene expression levels under a particular drug treatment. In each group, there may be several replicated measurements of the same treatment. First, one finds the within-group variance and the between-group variance. The within-group variance is the measurement variance of measurements within a treatment group. The between-group variance is the measurement variance of the means of different treatment groups. The within-group variance reflects the measurement error of the measurement technology, and the between-group variance includes both the measurement error of the measurement technology and the changes caused by different treatments. Then the between-group variance is compared to the within-group variance. If the between-group variance is significantly larger than the within-group variance, it may be concluded that the different treatments have produced statistically significant changes in gene expression levels. It is clear that in order to make this ANOVA method work optimally, the within-group variance (the measurement error) should be the same even when the measurement mean is different. In other words, the measurement error should be independent from the measurement level itself. Otherwise, the above comparison concept will not be valid. Therefore, in one embodiment, the invention provides a method for analyzing the variance in signals $\{x_i(k)\}$ measured in m experiments, wherein k=1, 2, . . . , N, N being the number of signals in each experiment, and i=1, 2, . . . , m being the number of experiments. In the method, the each signal $x_i(k)$ is transformed into a transformed signals $y_i(k)$ by a method comprising using a transformation described in Section 5.3. A normalized error in each of the transformed signal $y_i(k)$ is then determined. A statistical test, e.g., ANOVA, is then applied to one or more of the transformed signals $\{y_i(k)\}$ such that a variance for each of the one or more transformed signals is determined. In some embodiment, N=1. In preferred embodiments, N is at least 10, at least 100, at least 1000 or at least 10,000. In other preferred embodiments, m is at least 2, at least 5, at least 10, at least 100, at least 1000, or at least 10,000. In one embodiment, the m experiments are replicate experiments, e.g., m replicate microarray measurements of samples under a particular perturbation. In this embodiment, the variance as determined is the within-group variance. In another embodiment, the m experiments includes subgroups of experiments, each subgroup contains replicate experiments under a particular condition, e.g. m1 replicate microarray measurements of samples under a particular perturbation and m2=m−m1 replicate microarray measurements of samples under another perturbation different from the particular perturbation. In this embodiment, the variance as determined is the between-group variance. In this embodiment, the within-group variances for both m1 group and m2 group can also be determined by applying the method to signal data in groups m1 and m2, respectively.

5.4.2. Methods of Correcting Non-Linearity in Measured Signals

It has been demonstrated that microarray data often shows intensity dependent expression non-linearity when comparing treated and control samples, in both single-channel and two-channel technologies. Many data regression methods have been applied to estimate the non-linearity in order to correct it. Most of the known regression methods work best when the measurement variance is unrelated to the measurement quantity itself. Because of the intensity-dependant variance in microarray data, intensity transformation becomes necessary before data regression. The transformation as described in Section 5.3. provides optimal error characteristics for regression purposes in the non-linearity correction.

5.4.3. Methods of Obtaining Difference of Measured Signals

Measuring gene expression changes after a particular drug treatment is one of the most important tasks in microarray expression data analysis. Ratio (fold-change) or logarithmic ratio of a signal measured on, e.g. a sample treated by a drug, over a control signal, i.e., a signal measured on a control or untreated sample, e.g., measured in a two-channel measurement, is a commonly used method in the differential expression measurement. But because of the high error in the log-transformed low intensity data, large variance is observed in the log-ratio result near the low average intensity end. This is the so-called "fish tail"0 phenomenon in a typical log-ratio vs. average log-intensity plot, where the log-ratios at the low intensity end have much wider variations then those at the high intensity end (see FIG. 12). In addition, the ratio is not defined if either one of the intensities, i.e. from treated sample or from control sample, is negative. Negative intensities are common after background subtraction or in an experiment employing a perfect-match and mismatch scheme. In one embodiment, signals are first transformed by a transformation of Section 5.3, and differences between signals are then calculated in the transformed domain. Measured signals that can be analyzed by this methods include but not limited to measured expression levels obtained by the methods described in U.S. patent application Ser. No. 09/781,814, filed Feb. 12, 2001, by Shoemaker et al. or U.S. patent application Ser. No. 09/724,538, filed Nov. 28, 2001, by Shoemaker et al., each of which is incorporated herein by reference in its entirety for all purposes. Because the transformed intensities have the characteristics of constant variance, we can measure the difference rather than the ratio between the transformed intensities of the treated and control samples. The resulting difference has a near constant variance as well (see FIG. 13). Furthermore, the difference operation works in both positive and negative transformed intensities. At the high intensity end, the transformed intensity approximately equals the log intensity (see Equation 26), so that the difference approximately equals the natural-log ratio (log difference) by a factor of 1/a. At the low intensity end, the transformed intensity approximately equals the intensity itself because the first derivative is approximately a constant (see Equation 27).

Therefore, the difference of transformed intensities approximately equals the difference between the measured intensities by a factor of 1/c. These characteristics of signal differences in the transformed domain exhibit the advantages of both the regular intensity ratio computation (fold-change definition at high intensities) and the regular intensity difference computation (well defined and bounded noise at low and negative intensities). FIG. 12 and FIG. 13 are comparison examples of a traditional log-ratio plot and a difference plot in the transformed domain. The low-error benefit in the transformed difference at low intensity levels shown in FIG. 13 is especially helpful in detecting changes in weakly expressed genes. Many potential drug targets are often not highly expressed.

5.4.4. Methods of Obtaining Error-Weighted Signals

Error-weighted averaging has been used in combining replicated log-ratio microarray profiles that belong to the same experiment (see, e.g., PCT publication WO 00/39339, which is incorporated herein by reference in its entirety for all purposes). The weighing factor is inversely proportional to the ratio variance, so that the log-ratios having larger measurement errors contribute less to the averaged results. However, this weighting method should not be simply applied to intensity data, because the result will be biased to low intensity data that have lower absolute error than high intensity data. Thus, in one embodiment, intensity data $\{x(k)_i\}$, wherein k=1, 2, . . . , N, N being the number of signals measured, from the ith replicates are first transformed into a transformed domain $\{y(k)_i\}$ by a transformation of Section 5.3, e.g., a transformation according to equation 23. Preferably, in the transformation c is taken to be the averaged standard deviation obtained by averaging the standard deviation of all the replicate experiments. After the transformation, the error-weighted averaging can be carried out on the transformed intensity data whose variance is not related to the averaging quantity itself. In one embodiment, an error-weighted average in the transformed domain is determined according to the equation $$\overline{y}(k) = \frac{\sum_i (y(k)_i / \Delta y(k)_i^2)}{\sum_i (1 / \Delta y(k)_i^2)} \quad (31)$$

where i is the number of repeated measurements and $\Delta y(k)_i$ is the error in the transformed signal $y(k)_i$ (see, e.g., PCT publication WO 00/39339, which is incorporated herein by reference in its entirety for all purposes). The error-weighted averages are then transformed back by an inverse transformation, e.g., an inverse transformation as described by equation 25. By way of example, with error-weighted transformed intensity averaging, one can reduce the adverse effects caused by those low quality spots that have large measurement errors shown in FIG. 6 and FIG. 8.

5.4.5. Methods of Identifying and Removing Outliers

During the quality control (QC) process of microarray data analysis, it is important to identify and remove those signals generated by spots having unreliable measurements (such spots are also referred to as "outliers"). As shown in FIG. 6, many of these low quality spots have measurement errors that clearly are higher than most other spots. In one embodiment, measured signals are transformed into a transformed domain by a transformation of section 5.3. Because the transformed measurement error is not related to the measurement quantity (transformed intensity) itself, low quality outliers can be identified by simply setting an error threshold in the transformed domain and identifying spots with an error larger than the threshold as outliers. This can not be easily done if no transformation or other transformations are applied, where the variance is not approximately a constant.

5.5. Implementation Systems and Methods

The analytical methods of the present invention can preferably be implemented using a computer system, such as the computer system described in this section, according to the following programs and methods. Such a computer system can also preferably store and manipulate measured signals obtained in various experiments that can be used by a computer system implemented with the analytical methods of this invention. Accordingly, such computer systems are also considered part of the present invention.

An exemplary computer system suitable for implementing the analytic methods of this invention is illustrated in FIG. 14. Computer system 1401 is illustrated here as comprising internal components and as being linked to external components. The internal components of this computer system include one or more processor elements 1402 interconnected with a main memory 1403. For example, computer system 1401 can be an Intel Pentium®-based processor of 200 MHZ or greater clock rate and with 32 MB or more main memory. In a preferred embodiment, computer system 1401 is a cluster of a plurality of computers comprising a head "node" and eight sibling "nodes," with each node having a central processing unit ("CPU"). In addition, the cluster also comprises at least 128 MB of random access memory ("RAM") on the head node and at least 256 MB of RAM on each of the eight sibling nodes. Therefore, the computer systems of the present invention are not limited to those consisting of a single memory unit or a single processor unit.

The external components can include a mass storage 1404. This mass storage can be one or more hard disks that are typically packaged together with the processor and memory. Such hard disk are typically of 1 GB or greater storage capacity and more preferably have at least 6 GB of storage capacity. For example, in a preferred embodiment, described above, wherein a computer system of the invention comprises several nodes, each node can have its own hard drive. The head node preferably has a hard drive with at least 6 GB of storage capacity whereas each sibling node preferably has a hard drive with at least 9 GB of storage capacity. A computer system of the invention can further comprise other mass storage units including, for example, one or more floppy drives, one more CD-ROM drives, one or more DVD drives or one or more DAT drives.

Other external components typically include a user interface device 1405, which is most typically a monitor and a keyboard together with a graphical input device 1406 such as a "mouse." The computer system is also typically linked to a network link 1407 which can be, e.g., part of a local area network ("LAN") to other, local computer systems and/or part of a wide area network ("WAN"), such as the Internet, that is connected to other, remote computer systems. For example, in the preferred embodiment, discussed above, wherein the computer system comprises a plurality of nodes, each node is preferably connected to a network, preferably an NFS network, so that the nodes of the computer system communicate with each other and, optionally, with other computer systems by means of the network and can thereby share data and processing tasks with one another.

Loaded into memory during operation of such a computer system are several software components that are also shown schematically in FIG. 14. The software components comprise both software components that are standard in the art and components that are special to the present invention. These software components are typically stored on mass storage such as the hard drive 1404, but can be stored on other computer readable media as well including, for example, one or more floppy disks, one or more CD-ROMs, one or more DVDs or one or more DATs. Software component 1410 represents an operating system which is responsible for managing the computer system and its network interconnections. The operating system can be, for example, of the Microsoft Windows™ family such as Windows 95, Window 98, Windows NT or Windows 2000. Alternatively, the operating software can be a Macintosh operating system, a UNIX operating system or the LINUX operating system. Software components 1411 comprises common languages and functions that are preferably present in the system to assist programs implementing methods specific to the present invention. Languages that can be used to program the analytic methods of the invention include, for example, C and C++, FORTRAN, PERL, HTML, JAVA, and any of the UNIX or LINUX shell command languages such as C shell script language. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

Software component 1412 comprises any analytic methods of the present invention described supra, preferably programmed in a procedural language or symbolic package. For example, software component 1412 preferably includes programs that cause the processor to implement steps of accepting a plurality of measured signals and storing the measured signals in the memory. For example, the computer system can accept measured signals that are manually entered by a user (e.g., by means of the user interface). More preferably, however, the programs cause the computer system to retrieve measured signals from a database. Such a database can be stored on a mass storage (e.g., a hard drive) or other computer readable medium and loaded into the memory of the computer, or the compendium can be accessed by the computer system by means of the network 1407.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

5.6. Methods for Determining Biological State and Biological Response

This invention provides methods for analysis of measurement errors in measured signal data, e.g., measured expression profiles, and methods for analyzing and processing of such measured signal data. The measured signals can be measurements of cellular constituents in a cell or organism or responses of a cell or organism to a perturbation. The data can be measured from cell samples subject to different conditions, e.g., under different perturbations. The cell sample can be of any organism, e.g., eukaryote, mammal, primate, human, non-human animal such as a dog, cat, horse, cow, mouse, rat, *Drosophila, C. elegans*, etc., plant such as rice, wheat, bean, tobacco, etc., and fungi. The cell sample can be from a diseased or healthy organism, or an organism predisposed to disease. The cell sample can be of a particular tissue type or development stage or subjected to a particular perturbation (stimulus). This section and its subsections provides some exemplary methods for obtaining the measured signals of cell samples. One of skill in the art would appreciate that this invention is not limited to the following specific methods for measuring the expression profiles and responses of a biological system.

5.6.1. Transcript Assays using Microarrays

This invention is particularly useful for the determination of the expression state or the transcriptional state of a cell or cell type or any other cell sample by monitoring expression profiles. One aspect of the invention provides polynucleotide probe arrays for simultaneous determination of the expression levels of a plurality of genes and methods for designing and making such polynucleotide probe arrays.

The expression level of a nucleotide sequence in a gene can be measured by any high throughput techniques. However measured, the result is either the absolute or relative amounts of transcripts or response data, including but not limited to values representing abundance ratios.

Preferably, measurement of the expression profile is made by hybridization to transcript arrays, which are described in this subsection In a preferred embodiment, the present invention makes use of "transcript arrays" or "profiling arrays". Transcript arrays can be employed for analyzing the expression profile in a cell sample and especially for measuring the expression profile of a cell sample of a particular tissue type or developmental state or exposed to a drug of interest or to perturbations to a biological pathway of interest. In another embodiment, the cell sample can be from a patient, e.g., a diseased cell sample, and preferably can be compared to a healthy cell sample.

In one embodiment, an expression profile is obtained by hybridizing detectably labeled polynucleotides representing the nucleotide sequences in mRNA transcripts present in a cell (e.g., fluorescently labeled cDNA synthesized from total cell mRNA) to a microarray. A microarray is an array of positionally-addressable binding (e.g., hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways, of which several are described herein below. However produced, microarrays share certain characteristics. The arrays are reproducible, allowing multiple copies of a given array to be produced and easily compared with each other. Preferably, the microarrays are made from materials that are stable under binding (e.g., nucleic acid hybridization) conditions. The microarrays are preferably small, e.g., between about 1 cm$^2$ and 25 cm$^2$, preferably about 1 to 3 cm$^2$. However, both larger and smaller arrays are also contemplated and may be preferable, e.g., for simultaneously evaluating a very large number of different probes.

Preferably, a given binding site or unique set of binding sites in the microarray will specifically bind (e.g., hybridize) to a nucleotide sequence in a single gene from a cell or organism (e.g., to exon of a specific mRNA or a specific cDNA derived therefrom).

The microarrays used in the methods and compositions of the present invention include one or more test probes, each of which has a polynucleotide sequence that is complementary to a subsequence of RNA or DNA to be detected. Each probe preferably has a different nucleic acid sequence, and the position of each probe on the solid surface of the array is preferably known. Indeed, the microarrays are preferably addressable arrays, more preferably positionally addressable arrays. More specifically, each probe of the array is preferably located at a known, predetermined position on the solid support such that the identity (i.e., the sequence) of each probe can be determined from its position on the array (i.e., on the support or surface). In some embodiments of the invention, the arrays are ordered arrays.

Preferably, the density of probes on a microarray or a set of microarrays is about 100 different (i.e., non-identical) probes per 1 $cm^2$ or higher. More preferably, a microarray used in the methods of the invention will have at least 550 probes per 1 $cm^2$, at least 1,000 probes per 1 $cm^2$, at least 1,500 probes per 1 $cm^2$ or at least 2,000 probes per 1 $cm^2$. In a particularly preferred embodiment, the microarray is a high density array, preferably having a density of at least about 2,500 different probes per 1 $cm^2$. The microarrays used in the invention therefore preferably contain at least 2,500, at least 5,000, at least 10,000, at least 15,000, at least 20,000, at least 25,000, at least 50,000 or at least 55,000 different (i.e., non-identical) probes.

In one embodiment, the microarray is an array (i.e., a matrix) in which each position represents a discrete binding site for a nucleotide sequence of a transcript encoded by a gene (e.g., for an exon of an mRNA or a cDNA derived therefrom). The collection of binding sites on a microarray contains sets of binding sites for a plurality of genes. For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments of the present invention, a gene or an exon in a gene is represented in the profiling arrays by a set of binding sites comprising probes with different polynucleotides that are complementary to different coding sequence segments of the gene or an exon of the gene. Such polynucleotides are preferably of the length of 15 to 200 bases, more preferably of the length of 20 to 100 bases, most preferably 40-60 bases. It will be understood that each probe sequence may also comprise linker sequences in addition to the sequence that is complementary to its target sequence. As used herein, a linker sequence refers to a sequence between the sequence that is complementary to its target sequence and the surface of support. For example, in preferred embodiments the profiling arrays of the invention comprise one probe specific to each target gene or exon. However, if desired, the profiling arrays may contain at least 2, 5, 10, 100, 1000 probes specific to some target genes or exons. For example, the array may contain probes tiled across the sequence of the longest mRNA isoform of a gene at single base steps.

In specific embodiments of the invention, when an exon has alternative spliced variants, a set of polynucleotide probes of successive overlapping sequences, i.e., tiled sequences, across the genomic region containing the longest variant of an exon can be included in the exon profiling arrays. The set of polynucleotide probes can comprise successive overlapping sequences at steps of a predetermined base intervals, e.g. at steps of 1, 5, or 10 base intervals, span, or are tiled across, the mRNA containing the longest variant. Such set of probes therefore can be used to scan the genomic region containing all variants of an exon to determine the expressed variant or variants of the exon to determine the expressed variant or variants of the exon. Alternatively or additionally, a set of polynucleotide probes comprising exon specific probes and/or variant junction probes can be included in the exon profiling array. As used herein, a variant junction probe refers to a probe specific to the junction region of the particular exon variant and the neighboring exon. In a preferred embodiment, the probe set contains variant junction probes specifically hybridizable to each of all different splice junction sequences of the exon. In another preferred embodiment, the probe set contains exon specific probes specifically hybridizable to the common sequences in all different variants of the exon, and/or variant junction probes specifically hybridizable to the different splice junction sequences of the exon.

In some other embodiments of the invention, an exon is represented in the exon profiling arrays by a probe comprising a polynucleotide that is complementary to the full length exon. In such embodiments, an exon is represented by a single binding site on the profiling arrays. In some preferred embodiments of the invention, an exon is represented by one or more binding sites on the profiling arrays, each of the binding sites comprising a probe with a polynucleotide sequence that is complementary to an RNA fragment that is a substantial portion of the target exon. The lengths of such probes are normally between about 15-600 bases, preferably between about 20-200 bases, more preferably between about 30-100 bases, and most preferably between about 40-80 bases. The average length of an exon is about 200 bases (see, e.g., Lewin, *Genes V*, Oxford University Press, Oxford, 1994). A probe of length of about 40-80 allows more specific binding of the exon than a probe of shorter length, thereby increasing the specificity of the probe to the target exon. For certain genes, one or more targeted exons may have sequence lengths less than about 40-80 bases. In such cases, if probes with sequences longer than the target exons are to be used, it may be desirable to design probes comprising sequences that include the entire target exon flanked by sequences from the adjacent constitutively splice exon or exons such that the probe sequences are complementary to the corresponding sequence segments in the mRNAs. Using flanking sequence from adjacent constitutively spliced exon or exons rather than the genomic flanking sequences, i.e., intron sequences, permits comparable hybridization stringency with other probes of the same length. Preferably the flanking sequence used are from the adjacent constitutively spliced exon or exons that are not involved in any alternative pathways. More preferably the flanking sequences used do not comprise a significant portion of the sequence of the adjacent exon or exons so that cross-hybridization can be minimized. In some embodiments, when a target exon that is shorter than the desired probe length is involved in alternative splicing, probes comprising flanking sequences in different alternatively spliced mRNAs are designed so that expression level of the exon expressed in different alternatively spliced mRNAs can be measured.

In some other embodiments of the invention, when alternative splicing pathways and/or exon duplication in separate genes are to be distinguished, the DNA array or set of arrays can also comprise probes that are complementary to sequences spanning the junction regions of two adjacent exons. Preferably, such probes comprise sequences from the two exons which are not substantially overlapped with probes for each individual exons so that cross hybridization can be minimized. Probes that comprise sequences from more than one exons are useful in distinguishing alternative splicing pathways and/or expression of duplicated exons in separate genes if the exons occurs in one or more alternative spliced mRNAs and/or one or more separated genes that contain the duplicated exons but not in other alternatively spliced mRNAs and/or other genes that contain the duplicated exons. Alternatively, for duplicate exons in separate genes, if the exons from different genes show substantial difference in sequence homology, it is preferable to include probes that are different so that the exons from different genes can be distinguished.

It will be apparent to one skilled in the art that any of the probe schemes, supra, can be combined on the same profiling array and/or on different arrays within the same set of profiling arrays so that a more accurate determination of the expression profile for a plurality of genes can be accomplished. It will also be apparent to one skilled in the art that the different probe schemes can also be used for different levels of accuracies in profiling. For example, a profiling array or array set comprising a small set of probes for each exon may be used to determine the relevant genes and/or RNA splicing pathways under certain specific conditions. An array or array set comprising larger sets of probes for the exons that are of interest is then used to more accurately determine the exon expression profile under such specific conditions. Other DNA array strategies that allow more advantageous use of different probe schemes are also encompassed.

Preferably, the microarrays used in the invention have binding sites (i.e., probes) for sets of exons for one or more genes relevant to the action of a drug of interest or in a biological pathway of interest. As discussed above, a "gene" is identified as a portion of DNA that is transcribed by RNA polymerase, which may include a 5' untranslated region ("UTR"), introns, exons and a 3' UTR. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the genome of *Saccharomyces cerevisiae* has been completely sequenced and is reported to have approximately 6275 ORFs encoding sequences longer the 99 amino acid residues in length. Analysis of these ORFs indicates that there are 5,885 ORFs that are likely to encode protein products (Goffeau et al., 1996, *Science* 274:546-567). In contrast, the human genome is estimated to contain approximately 30,000 to 130,000 genes (see Crollius et al., 2000, *Nature Genetics* 25:235-238; Ewing et al., 2000, *Nature Genetics* 25:232-234). Genome sequences for other organisms, including but not limited to *Drosophila, C. elegans*, plants, e.g., rice and Arabidopsis, and mammals, e.g., mouse and human, are also completed or nearly completed. Thus, in preferred embodiments of the invention, an array set comprising in total probes for all known or predicted exons in the genome of an organism is provided. As a non-limiting example, the present invention provides an array set comprising one or two probes for each known or predicted exon in the human genome.

It will be appreciated that when cDNA complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In preferred embodiments, cDNAs from cell samples from two different conditions are hybridized to the binding sites of the microarray using a two-color protocol. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA derived from each of the two cell types are differently labeled (e.g., with Cy3 and Cy5) so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, change the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467-470, which is incorporated by reference in its entirety for all purposes. The scheme is equally applicable to labeling and detection of exons. An advantage of using cDNA labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell. Furthermore, labeling with more than two colors is also contemplated in the present invention. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

In some embodiments of the invention, hybridization data are measured at a plurality of different hybridization times so that the evolution of hybridization levels to equilibrium can be determined. In such embodiments, hybridization levels are most preferably measured at hybridization times spanning the range from 0 to in excess of what is required for sampling of the bound polynucleotides (i.e., the probe or probes) by the labeled polynucleotides so that the mixture is close to or substantially reached equilibrium, and duplexes are at concentrations dependent on affinity and abundance rather than diffusion. However, the hybridization times are preferably short enough that irreversible binding interactions between the labeled polynucleotide and the probes and/or the surface do not occur, or are at least limited. For example, in embodiments wherein polynucleotide arrays are used to probe a complex mixture of fragmented polynucleotides, typical hybridization times may be approximately 0-72 hours. Appropriate hybridization times for other embodiments will depend on the particular polynucleotide sequences and probes used, and may be determined by those skilled in the art (see, e.g., Sambrook et al., Eds., 1989, *Molecular Cloning: A Laboratory Manual*, 2nd ed., Vol. 1-3, Cold Spring Harbor Laboratory, Cold Spring Harbor, N.Y.).

In one embodiment, hybridization levels at different hybridization times are measured separately on different, identical microarrays. For each such measurement, at hybridization time when hybridization level is measured, the microarray is washed briefly, preferably in room temperature in an aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used. The resulted hybridization levels are then combined to form a hybridization curve. In another embodiment, hybridization levels are measured in real time using a single microarray. In this embodiment, the microarray is allowed to hybridize to the sample without interruption and the microarray is interrogated at each hybridization time in a non-invasive manner. In still another embodiment, one can use one array, hybridize for a short time, wash and measure the hybridization level, put back to the same sample, hybridize for another period of time, wash and measure again to get the hybridization time curve.

Preferably, at least two hybridization levels at two different hybridization times are measured, a first one at a hybridization time that is close to the time scale of cross-hybridization equilibrium and a second one measured at a hybridization time that is longer than the first one. The time scale of cross-hybridization equilibrium depends, inter alia, on sample composition and probe sequence and may be determined by one skilled in the art. In preferred embodiments, the first hybridization level is measured at between 1 to 10 hours, whereas the second hybridization time is measured at about 2, 4, 6, 10, 12, 16, 18, 48 or 72 times as long as the first hybridization time.

5.6.2. Preparing Probes for Microarrays

As noted above, the "probe" to which a particular polynucleotide molecule, such an exon, specifically hybridizes according to the invention is a complementary polynucleotide sequence. Preferably one or more probes are selected for each target exon. For example, when a minimum number of probes are to be used for the detection of an exon, the probes normally comprise nucleotide sequences greater than about 40 bases in length. Alternatively, when a large set of redundant probes is to be used for an exon, the probes normally comprise nucleotide sequences of about 40-60 bases. The probes can also comprise sequences complementary to full length exons. The lengths of exons can range from less than 50 bases to more than 200 bases. Therefore, when a probe length longer than exon is to be used, it is preferable to augment the exon sequence with adjacent constitutively spliced exon sequences such that the probe sequence is complementary to the continuous mRNA fragment that contains the target exon. This will allow comparable hybridization stringency among the probes of an exon profiling array. It will be understood that each probe sequence may also comprise linker sequences in addition to the sequence that is complementary to its target sequence.

The probes may comprise DNA or DNA "mimics" (e.g., derivatives and analogues) corresponding to a portion of each exon of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of exon segments from genomic DNA, cDNA (e.g., by RT-PCR), or cloned sequences. PCR primers are preferably chosen based on known sequence of the exons or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehier et al., 1986, *Nucleic Acid Res.* 14:5399-5407; McBride et al., 1983, *Tetrahedron Lett.* 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 365:566-568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207-209).

5.6.3. Attaching Probes to the Solid Surface

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

A preferred method for attaching the nucleic acids to a surface is by printing on glass plates, as is described generally by Schena et al, 1995, *Science* 270:467-470. This method is especially useful for preparing microarrays of cDNA (See also, DeRisi et al, 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

A second preferred method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al., 1994, *Proc. Natl. Acad. Sci. U.S.A.* 91:5022-5026; Lockhart et al, 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). When these methods are used, oligonucleotides (e.g., 60-mers) of known sequence are synthesized directly on a surface such as a derivatized glass slide. The array produced can be redundant, with several polynucleotide molecules per exon.

Other methods for making microarrays, e.g., by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123; and U.S. Pat. No. 6,028,189 to Blanchard. Specifically, the polynucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Polynucleotide probes are normally attached to the surface covalently at the 3' end of the polynucleotide. Alternatively, polynucleotide probes can be attached to the surface covalently at the 5' end of the polynucleotide (see for example, Blanchard, 1998, in *Synthetic DNA Arrays in Genetic Engineering*, Vol. 20, J. K. Setlow, Ed., Plenum Press, New York at pages 111-123).

5.6.4. Target Polynucleotide Molecules

Target polynucleotides which may be analyzed by the methods and compositions of the invention include RNA molecules such as, but by no means limited to messenger RNA (mRNA) molecules, ribosomal RNA (rRNA) molecules, cRNA molecules (i.e., RNA molecules prepared from cDNA molecules that are transcribed in vivo) and fragments thereof. Target polynucleotides which may also be analyzed by the methods and compositions of the present invention include, but are not limited to DNA molecules such as genomic DNA molecules, cDNA molecules, and fragments thereof including oligonucleotides, ESTs, STSs, etc.

The target polynucleotides may be from any source. For example, the target polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian cells, the target polynucleotides may correspond to particular fragments of a gene transcript. For example, the target polynucleotides may correspond to different exons of the same gene, e.g., so that different splice variants of that gene may be detected and/or analyzed.

In preferred embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation and an oligo dT purification (Chirgwin et al., 1979, *Biochemistry* 18:5294-5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In preferred embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891,636, 5,716,785; 5,545,522 and 6,132,997; see also, U.S. patent application Ser. No. 09/411,074, filed Oct. 4, 1999 by Linsley and Schelter and U.S. Provisional Patent Application Ser. No. 60/253,641, filed on Nov. 28, 2000, by Ziman et al.). Both oligo-dT primers (U.S. Pat. Nos. 5,545,522 and 6,132,997) or random primers (U.S. Provisional Patent Application Serial No. 60/253,641, filed on Nov. 28, 2000, by Ziman et al.) that contain an RNA polymerase promoter or complement thereof can be used. Preferably, the target polynucleotides are short and/or fragmented polynucleotide molecules which are representative of the original nucleic acid population of the cell.

The target polynucleotides to be analyzed by the methods and compositions of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}P$, $^{35}S$, $^{14}C$, $^{15}N$ and 125I. Fluorescent molecules suitable for the present invention include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41. Fluorescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.6.5. Hybridization to Microarrays

As described supra, nucleic acid hybridization and wash conditions are chosen so that the polynucleotide molecules to be analyzed by the invention (referred to herein as the "target polynucleotide molecules") specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93.10614). Useful hybridization conditions are also provided in, e.g., Tijessen, 1993, *Hybridization With Nucleic Acid Probes*, Elsevier Science Publishers B. V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

5.6.6. Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced by from the same gene by alternative splicing is then determined by the signal strength pattern across the whole set of exons monitored for the gene.

In preferred embodiments, target sequences, e.g., cDNAs or cRNAs, from two different cells are hybridized to the binding sites of the microarray. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA or cRNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, changes the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467-470, which is incorporated by reference in its entirety for all purposes. The scheme is equally applicable to labeling and detection of exons. An advantage of using target sequences, e.g., cDNAs or cRNAs, labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell.

In other preferred embodiments, single-channel detection methods, e.g., using one-color fluorescence labeling, are used (see U.S. provisional patent application Serial No. 60/227, 966, filed on Aug. 25, 2000). In this embodiment, arrays comprising reverse-complement (RC) probes are designed and produced. Because a reverse complement of a DNA sequence has sequence complexity that is equivalent to the corresponding forward-strand (FS) probe that is complementary to a target sequence with respect to a variety of measures (e.g., measures such as GC content and GC trend are invariant under the reverse complement), a RC probe is used to as a control probe for determination of level of non-specific cross hybridization to the corresponding FS probe. The significance of the FS probe intensity of a target sequence is determined by comparing the raw intensity measurement for the FS probe and the corresponding raw intensity measurement for the RC probe in conjunction with the respective measurement errors. In a preferred embodiment, an exon is called present if the intensity difference between the FS probe and the corresponding RC probe is significant. More preferably, an exon is called present if the FS probe intensity is also significantly above background level. Single-channel detection methods can be used in conjunction with multi-color labeling. In one embodiment, a plurality of different samples, each labeled with a different color, is hybridized to an array. Differences between FS and RC probes for each color are used to determine the level of hybridization of the corresponding sample.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639-645. Alternatively, the fiber-optic bundle described by Ferguson et al., 1996, *Nature Biotech.* 14:1681-1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA and/or an exon expressed in an mRNA in two cells or cell lines is scored as perturbed (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of difference of an order of about 3-fold to about 5-fold, but more sensitive methods are expected to be developed.

It is, however, also advantageous to determine the magnitude of the relative difference in abundances for an mRNA and/or an exon expressed in an mRNA in two cells or in two cell lines. This can be carried out, as noted above, by calculating the ratio of the emission of the two fluorophores used for differential labeling, or by analogous methods that will be readily apparent to those of skill in the art.

5.6.7. Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, *Proc. Natl. Acad. Sci. USA* 93:659-663). Other methods statistically sample cDNA pools, such as by sequencing sufficient bases (e.g., 20-50 bases) in each of multiple cDNAs to identify each cDNA, or by sequencing short tags (e.g., 9-10 bases) that are generated at known positions relative to a defined mRNA end (see, e.g., Velculescu, 1995, *Science* 270:484-487).

5.7. Measurement of Other Aspects of the Biological State

In various embodiments of the present invention, aspects of the biological state other than the transcriptional state, such as the translational state, the activity state, or mixed aspects can be measured to produce the measured signals to be analyzed according to the invention. Thus, in such embodiments, gene expression data may include translational state measurements or even protein expression measurements. In fact, in some embodiments, rather than using gene expression interaction maps based on gene expression, protein expression interaction maps based on protein expression maps are used. Details of embodiments in which aspects of the biological state other than the transcriptional state are described in this section.

5.7.1. Embodiments Based on Translational State Measurements

Measurement of the translational state may be performed according to several methods. For example, whole genome monitoring of protein (i.e., the "proteome," Goffeau et al., 1996, *Science* 274:546-567; Gygi et al., 1999, Nature Biotechnology 17:994-999) can be carried out by constructing a microarray in which binding sites comprise immobilized, preferably monoclonal, antibodies specific to a plurality of protein species encoded by the cell genome (see, e.g., Zhu et al., 2001, Science 293:2101-2105; MacBeath et al., 2000, Science 289:1760-63; de Wildt et al., 2000, Nature Biotechnology 18:989-994). Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, New York, which is incorporated in its entirety for all purposes). In a preferred embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated and measured by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Natl. Acad. Sci. USA* 93:1440-1445; Sagliocco et al., 1996, *Yeast* 12:1519-1533; Lander, 1996, *Science* 274:536-539; and Beaumont et al., Life Science News June, 2001, Amersham Pharmacia Biotech. The resulting electropherograms can be analyzed by numerous techniques, including mass spectrometric techniques, Western blotting and immunoblot analysis using polyclonal and monoclonal antibodies, and internal and N-terminal microsequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

5.7.2. Embodiments Based on Other Aspects of the Biological State

Even though methods of this invention are illustrated by embodiments involving gene expression, the methods of the invention are applicable to any cellular constituent that can be monitored. In particular, where activities of proteins can be measured, embodiments of this invention can use such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In alternative and non-limiting embodiments, response data may be formed of mixed aspects of the biological state of a cell. Response data can be constructed from, e.g., changes in certain mRNA abundances, changes in certain protein abundances, and changes in certain protein activities.

5.8. Measurement of Drug Response Data

Drug responses are obtained for use in the instant invention by measuring the gene expression state changed by drug exposure. The biological response described on the exon level can also be measured by exon profiling methods. The measured response data include values representing gene expression level values or gene expression level ratios for a plurality of genes.

To measure drug response data, cell can be exposed to graded levels of the drug or drug candidate of interest. When the cells are grown in vitro, the compound is usually added to their nutrient medium. The drug is added in a graded amount that depends on the particular characteristics of the drug, but usually will be between about 1 ng/ml and 100 mg/ml. In some cases a drug will be solubilized in a solvent such as DMSO.

The exon expression profiles of cells exposed to the drug and of cells not exposed to the drug are measured according to the methods described in the previous section. Preferably, gene transcript arrays are used to find the genes with altered gene expression profiles due to exposure to the drug.

It is preferable for measurements of drug responses, in the case of two-colored differential hybridization described above, to measure with reversed labeling. Also, it is preferable that the levels of drug exposure used provide sufficient resolution of rapidly changing regions of the drug response, e.g., by using approximately ten levels of drug exposure.

5.9. Methods for Probing Biological States

One aspect of the invention provides methods for the analysis of biological state. The methods of this invention are also useful for the analysis of responses of a cell sample to perturbations designed to probe cellular state. Preferred perturbations are those that cause a change in the amount of alternative splicing that occurs in one or more RNA transcripts. This section provides some illustrative methods for probing gene expression states and protein abundances and acitivities. See PCT publication WO 00/24936 for more detailed descriptions of these method.

Methods for targeted perturbation of cells are widely known and applied in the art. For example, such methods include use of titratable expression systems, use of transfection or viral transduction systems, direct modifications to RNA abundances or activities, direct modifications of protein abundances, direct modification of protein activities including use of drugs (or chemical moieties in general), and post-transcriptional gene silencing (PTGS) or RNA interference (RNAi).

In mammalian cells, several means of titrating expression of genes are available (Spencer, 1996, Trends Genet. 12:181-187). For example, the Tet system is widely used, both in its original form, the "forward" system, in which addition of doxycycline represses transcription, and in the newer "reverse" system, in which doxycycline addition stimulates transcription (Gossen et al., 1995, Proc. Natl. Acad. Sci. USA 89:5547-5551; Hoffmann et al., 1997, Nucl. Acids. Res. 25:1078-1079; Hofmann et al., 1996, Proc. Natl. Acad. Sci. USA 83:5185-5190; Paulus et al., 1996, Journal of Virology 70:62-67). Another commonly used controllable promoter system in mammalian cells is the ecdysone-inducible system developed by Evans and colleagues (No et al., 1996, Proc. Nat. Acad. Sci. USA 93:3346-3351), where expression is controlled by the level of muristerone added to the cultured cells. Finally, expression can be modulated using the "chemical-induced dimerization" (CID) system developed by Schreiber, Crabtree, and colleagues (Belshaw et al., 1996, Proc. Nat. Acad. Sci. USA 93:4604-4607; Spencer, 1996, Trends Genet. 12:181-187) and similar systems in yeast. In this system, the gene of interest is put under the control of the CID-responsive promoter, and transfected into cells expressing two different hybrid proteins, one comprised of a DNA-binding domain fused to FKBP12, which binds FK506. The other hybrid protein contains a transcriptional activation domain also fused to FKBP12. The CID inducing molecule is FK1012, a homodimeric version of FK506 that is able to bind simultaneously both the DNA binding and transcriptional activating hybrid proteins. In the graded presence of FK1012, graded transcription of the controlled gene is activated.

Transfection or viral transduction of target genes can introduce controllable perturbations in biological gene expression states in mammalian cells. Preferably, transfection or transduction of a target gene can be used with cells that do not naturally express the target gene of interest. Such non-expressing cells can be derived from a tissue not normally expressing the target gene or the target gene can be specifically mutated in the cell. The target gene of interest can be cloned into one of many mammalian expression plasmids, for example, the pcDNA3.1 ± system (Invitrogen, Inc.) or retroviral vectors, and introduced into the non-expressing host cells. Transfected or transduced cells expressing the target gene may be isolated by selection for a drug resistance marker encoded by the expression vector. The level of gene transcription is monotonically related to the transfection dosage. In this way, the effects of varying levels of the target gene may be investigated. Other methods of modifying RNA abundances and activities and thus gene abundances include ribozymes, antisense species, and RNA aptamers (Good et al., 1997, Gene Therapy 4: 45-54). Controllable application or exposure of a cell to these entities permits controllable perturbation of RNA abundances.

Ribozymes are RNAs which are capable of catalyzing RNA cleavage reactions. (Cech, 1987, Science 236:1532-1539; PCT International Publication WO 90/11364, published Oct. 4, 1990; Sarver et al., 1990, Science 247: 1222-1225). "Hairpin" and "hammerhead" RNA ribozymes can be designed to specifically cleave a particular target mRNA. Rules have been established for the design of short RNA molecules with ribozyme activity, which are capable of cleaving other RNA molecules in a highly sequence specific way and can be targeted to virtually all kinds of RNA. (Haseloff et al., 1988, Nature 334:585-591; Koizumi et al., 1988, FEBS Lett., 228:228-230; Koizumi et al., 1988, FEBS Lett., 239: 285-288). Ribozyme methods involve exposing a cell to, inducing expression in a cell, etc. of such small RNA ribozyme molecules. (Grassi and Marini, 1996, Annals of Medicine 28: 499-510; Gibson, 1996, Cancer and Metastasis Reviews 15: 287-299).

In another embodiment, activity of a target RNA (preferable mRNA) species, specifically its rate of translation, can be controllably inhibited by the controllable application of antisense nucleic acids. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered in a controllable manner to a cell or which can be produced intracellularly by transcription of exogenous, introduced sequences in controllable quantities sufficient to perturb translation of the target RNA.

In still another embodiment, RNA aptamers can be introduced into or expressed in a cell. RNA aptamers are specific RNA ligands for proteins, such as for Tat and Rev RNA (Good et al., 1997, Gene Therapy 4: 45-54) that can specifically inhibit their translation.

Post-transcriptional gene silencing (PTGS) or RNA interference (RNAi) can also be used to modify RNA abundances (Guo et al., 1995, Cell 81:611-620; Fire et al., 1998, Nature 391:806-811). In RNAi, dsRNAs are injected into cells to specifically block expression of its homologous gene. In particular, in RNAi, both the sense strand and the anti-sense strand can inactivate the corresponding gene. It is suggested that the dsRNAs are cut by nuclease into 21-23 nucleotide fragments. These fragments hybridize to the homologous region of their corresponding mRNAs to form double-stranded segments which are degraded by nuclease (Grant, 1999, Cell 96:303-306; Tabara et al., 1999, Cell 99:123-132; Zamore et al., 2000, Cell 101:25-33; Bass, 2000, Cell 101: 235-238; Petcherski et al., 2000, Nature 405:364-368; Elbashir et al., Nature 411:494-498; Paddison et al., Proc. Natl. Acad. Sci. USA 99:1443-1448; Technical Bulletins at the web site http://www.dharmacon.con/tech/tech03.html, accessed Oct. 16, 2001;). Therefore, in one embodiment, one or more dsRNAs having sequences homologous to the sequences of one or more mRNAs whose abundances are to be modified are transfected into a cell or tissue sample. Any standard method for introducing nucleic acids into cells can be used.

Methods of modifying protein abundances include, inter alia, those altering protein degradation rates and those using antibodies (which bind to proteins affecting abundances of activities of native target protein species). Increasing (or decreasing) the degradation rates of a protein species decreases (or increases) the abundance of that species. Methods for controllably increasing the degradation rate of a target protein in response to elevated temperature and/or exposure to a particular drug, which are known in the art, can be employed in this invention. For example, one such method employs a heat-inducible or drug-inducible N-terminal degron, which is an N-terminal protein fragment that exposes a degradation signal promoting rapid protein degradation at a higher temperature (e.g., 37° C.) and which is hidden to prevent rapid degradation at a lower temperature (e.g., 23° C.) (Dohmen et. al, 1994, Science 263:1273-1276). Such an exemplary degron is Arg-DHFR$^{ts}$, a variant of murine dihydrofolate reductase in which the N-terminal Val is replaced by Arg and the Pro at position 66 is replaced with Leu. According to this method, for example, a gene for a target protein, P, is replaced by standard gene targeting methods known in the art (Lodish et al., 1995, *Molecular Biology of the Cell*, W. H. Freeman and Co., New York, especially chap 8) with a gene coding for the fusion protein Ub-Arg-DHFR$^{ts}$-P ("Ub" stands for ubiquitin). The N-terminal ubiquitin is rapidly cleaved after translation exposing the N-terminal degron. At lower temperatures, lysines internal to Arg-DHFR$^{ts}$ are not exposed, ubiquitination of the fusion protein does not occur, degradation is slow, and active target protein levels are high. At higher temperatures (in the absence of methotrexate), lysines internal to Arg-DHFR$^{ts}$ are exposed, ubiquitination of the fusion protein occurs, degradation is rapid, and active target protein levels are low. Heat activation of degradation is controllably blocked by exposure methotrexate. This method is adaptable to other N-terminal degrees which are responsive to other inducing factors, such as drugs and temperature changes.

Methods of directly modifying protein activities include, inter alia, dominant negative mutations, specific drugs or chemical moieties generally, and also the use of antibodies.

6. EXAMPLE: TEST RESULTS

The following example is presented by way of illustration of the present invention, and is not intended to limit the present invention in any way.

Figure 4:
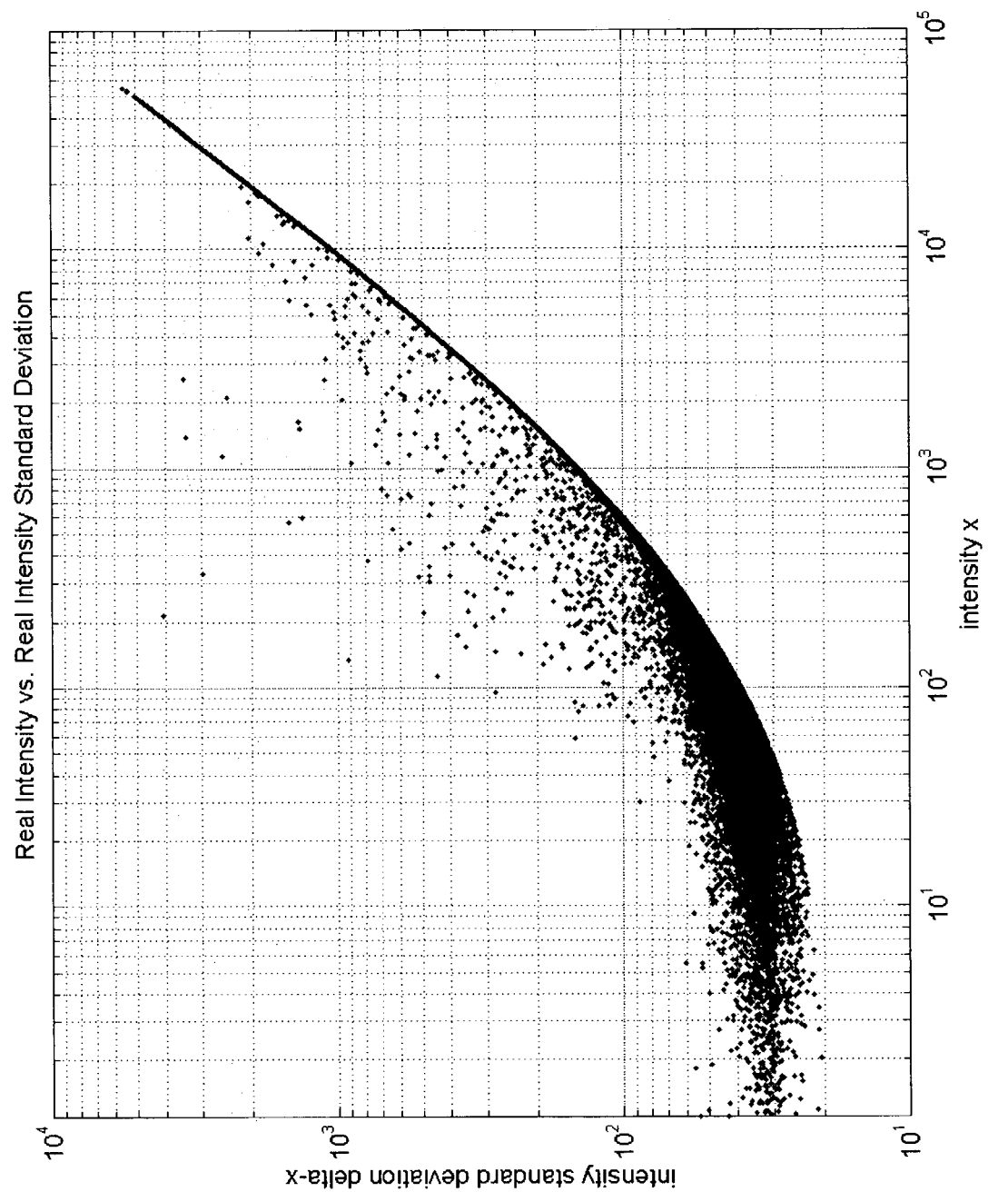
FIG. 4 is a plot of the relationship between the intensity x and the estimated real intensity standard deviation $\Delta x$ from a real testing microarray. Parameters used in Equation 8 for the modeled error are a=0.1, b=3.16, and c=30.1.

FIG. 4 shows an exemplary plot of a typical microarray intensity x vs. its approximated real standard deviation $\Delta x$. The approximated $\Delta x$ was estimated by taking the larger of the measured standard error of the mean spot intensity that was computed from pixel intensities in the spot and the modeled error using Equation 8. The smooth bottom contour of $\Delta x$ in the plot is the result of the larger conservative error estimate provided by Equation 8. In the middle intensity range, scatters that have $\Delta x$ much higher than the smooth error bottom contour are those having large standard errors in the intensity measurements. These spots are usually contaminated or mechanically damaged, many of which often are not removed during microarray image analysis. In FIG. 4, there are few scatters above the bottom contour at the high intensity end. This is because at the high intensity end pixel intensities are saturated and the measured standard error tends to underestimate the real error. Data shown in FIG. 4 were used in the following tests.

Figure 5:
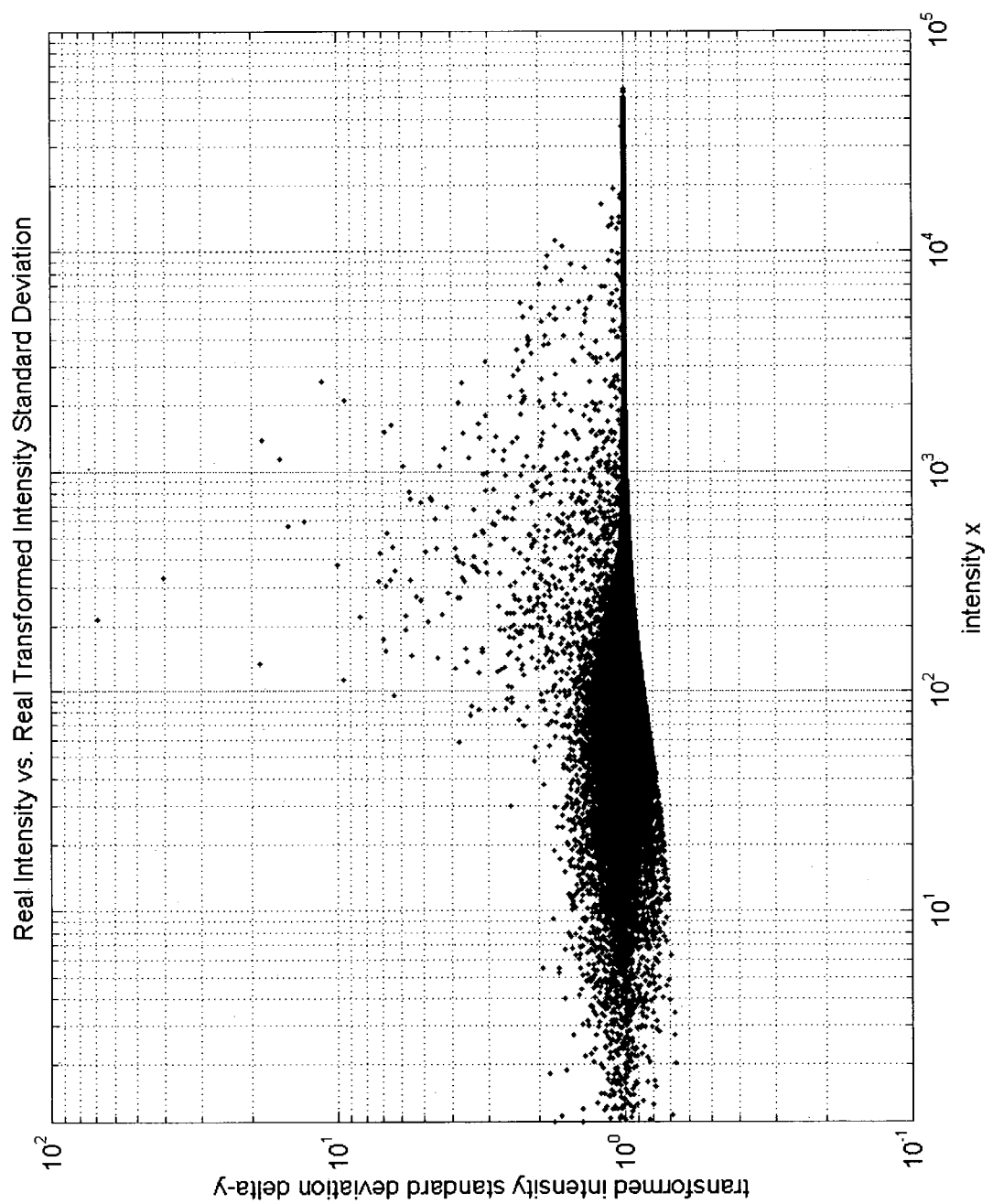
FIG. 5 is a plot of the relationship between the intensity x and the estimated real transformed intensity standard deviation $\Delta y$ from a real testing microarray. Parameters in the transformation are a=0.1, b=3.16, c=30.1 and d=−50.8.

FIG. 5 is a plot of the measured intensity x vs. the standard deviation $\Delta y$ of transformed intensity. FIG. 6 is an error characteristics plot of the transformed intensity y vs. $\Delta y$. In both plots, one can see that the transformed real standard deviation $\Delta y$ is distributed around constant one. Thus, there is a constant variance property in the transformed domain.

In comparison, the error characteristics plot of the hybrid transformation is shown in FIG. 7. It is clear that the hybrid transformation does not provide the desired property of constant variance. The result of logarithmic transformation is not shown, because it is much worse than the hybrid transformation at the low intensity end.

FIG. 8 is an example of the error characteristics of the transformed PM-MM intensity vs. the transformed error. The variance is still near a constant across the entire transformed intensity range of both positive and negative. Scatters that have high variance near the zero transformed PM-MM intensity area are those having high non-specific hybridization in both PM and MM. Although the difference of PM intensity minus MM intensity is small, the large measurement error from the high PM and MM intensities still remains after the subtraction. FIG. 9 is a histogram plot of the transformed PM-MM intensities. The transformed intensity distribution maintains the general smooth unimodal shape in the original PM-MM intensity distribution of a typical microarray (not shown).

In comparison, FIG. 10 and FIG. 11 are the hybrid-transformed PM-MM error characteristics and intensity distribution. The intensity-dependent error trend in the hybrid transformation is demonstrated in the error-characteristics plot. The lack of smoothness of the piecewise hybrid transformation also causes the significant intensity distribution distortion near the transition boundary c'.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for analyzing measurement errors in a set of measured signals $\{x(k)\}$ measured in an experiment, wherein $k=1, 2, \ldots, N$, N being the number of signals in said set, said method comprising
    (a) transforming said set of measured signals using a transformation, said transformation transforming said set of measured signals into a set of transformed signals $\{y(k)\}$ such that said transformed signals have a near constant error; and
    (b) determining error in each of said transformed signals by normalizing measurement error in said measured signal by a modeled error in said measured signal, said modeled error being calculated using an error model of said experiment; and
    (c) outputting said set of transformed signals and/or said errors determined in step (b) to a user interface device, a computer readable storage medium, or a local or remote computer system; or displaying said set of transformed signals and/or said errors determined in step (b).

2. The method of claim 1, wherein said error model is a three-term error model according to the equation $$\sigma_x(k) = \sqrt{c^2 + b^2 \cdot x(k) + a^2 \cdot x(k)^2}$$

wherein a is the fractional error coefficient of said experiment, b is the Poisson error coefficient of said experiment, and c is the standard deviation of background noise of said experiment.

3. The method of claim 2, wherein for each measured signal $x(k)$ said transformation is carried out according to the equation $$y(k) = \frac{\ln\left(\frac{b^2 + 2 \cdot a^2 \cdot x(k)}{a} + 2 \cdot \sqrt{c^2 + b^2 \cdot x(k) + a^2 \cdot x(k)^2}\right)}{a} + d,$$

wherein $$d = \frac{-\ln\left(\frac{b^2}{a} + 2 \cdot c\right)}{a}.$$

4. The method of claim 3, wherein for each measured signal $x(k)$ said error of said transformed signal $y(k)$ is determined according to the equation $$\Delta y(k) = \frac{\Delta x(k)}{\sqrt{c^2 + b^2 \cdot x(k) + a^2 \cdot x(k)^2}}$$

wherein $\Delta y(k)$ is said error in said transformed signal $y(k)$, and wherein $\Delta x(k)$ is an error in said measured signal $x(k)$.

5. The method of claim 4, wherein for each measured signal $x(k)$ said error in said measured signal $x(k)$ is an error in said measured signal $x(k)$ determined in said experiment.

6. The method of claim 5, wherein for each measured signal $x(k)$ said error in said measured signal $x(k)$ is the larger of an error in said measured signal $x(k)$ determined in said experiment or said modeled error in said measured signal $x(k)$.

7. The method of claim 1, further comprising before said step (a) the steps of
    (i) determining said error model for said experiment;
    (ii) determining said modeled error in each of said measured signals; and
    (iii) determining said transformation for said experiment.

8. The method of claim 7, wherein said error model is a three-term error model according to the equation $$\sigma_x(k) = \sqrt{c^2 + b^2 \cdot x(k) + a^2 \cdot x(k)^2}$$

wherein a is the fractional error coefficient of said experiment, b is the Poisson error coefficient of said experiment, and c is the standard deviation of background noise of said experiment.

9. The method of claim 8, wherein for each measured signal $x(k)$ said transformation is carried out according to the equation $$y(k) = \frac{\ln\left(\frac{b^2 + 2 \cdot a^2 \cdot x(k)}{a} + 2 \cdot \sqrt{c^2 + b^2 \cdot x(k) + a^2 \cdot x(k)^2}\right)}{a} + d,$$

wherein $$d = \frac{-\ln\left(\frac{b^2}{a} + 2 \cdot c\right)}{a}.$$

10. The method of claim 9, wherein for each measured signal $x(k)$ said error of said transformed signal $y(k)$ is determined according to the equation $$\Delta y(k) = \frac{\Delta x(k)}{\sqrt{c^2 + b^2 \cdot x(k) + a^2 \cdot x(k)^2}}$$

wherein $\Delta y(k)$ is said error in said transformed signal $y(k)$, and wherein $\Delta x(k)$ is an error in said measured signal $x(k)$.

11. The method of claim 10, wherein for each measured signal $x(k)$ said error in said measured signal $x(k)$ is an error in said measured signal $x(k)$ determined in said experiment.

12. The method of claim 10, wherein for each measured signal $x(k)$ said error in said measured signal $x(k)$ is the larger of an error in said measured signal $x(k)$ determined in said experiment or said modeled error in said measured signal $x(k)$.

13. A method for determining a residue error in a measured signal x measured in an experiment, said method comprising
    (a) transforming said measured signal into a transformed signal y by a method comprising using a transformation according to the equation $$y = \frac{\ln\left(\frac{b^2 + 2 \cdot a^2 \cdot x}{a} + 2 \cdot \sqrt{c^2 + b^2 \cdot x + a^2 \cdot x^2}\right)}{a} + d,$$

wherein a is the fractional error coefficient of said experiment, b is the Poisson error coefficient of said experiment, and c is the standard deviation of background noise of said experiment, and $$d = \frac{-\ln\left(\frac{b^2}{a} + 2 \cdot c\right)}{a}$$

(b) determining an error in said transformed signal y;

(c) determining said residue error by subtracting 1 from said error of said transformed signal y; and (d) outputting said residue error to a user interface device, a computer readable storage medium, or a local or remote computer system; or displaying said residue error.

14. The method of claim 13, wherein said error of said transformed signal y is determined according to the equation $$\Delta y = \frac{\Delta x}{\sqrt{c^2 + b^2 \cdot x + a^2 \cdot x^2}};$$

wherein $\Delta y$ is said error in said transformed signal y, and wherein $\Delta x$ is an error in said measured signal x.

15. The method of claim 14, wherein said error in said measured signal x is an error in said measured signal x determined in said experiment.

16. The method of claim 14, wherein said error in said measured signal x is the larger of an error determined in said experiment or an error calculated according to the equation $$\Delta x = \sqrt{c^2 + b^2 \cdot x + a^2 \cdot x^2}.$$

17. A method for determining an error-weighted average of m signals $x_i$ measured in m replicate experiments, wherein i=1, 2, . . . m, said method comprising (a) transforming each said signal $x_i$ into a transformed signal $y_i$ by a method comprising using a transformation $$y_i = \frac{\ln\left(\frac{b^2 + 2 \cdot a^2 \cdot x_i}{a} + 2 \cdot \sqrt{c^2 + b^2 \cdot x_i + a^2 \cdot x_i^2}\right)}{a} + d,$$

wherein a is the fractional error coefficient of said experiments, b is the Poisson error coefficient of said experiments, and c is the averaged standard deviation of background noise of said experiments, and $$d = \frac{-\ln\left(\frac{b^2}{a} + 2 \cdot c\right)}{a};$$

(b) determining an error $\Delta y_i$ in each said transformed signal $y_1$;

(c) determining an error-weighted transformed signal according to the equation $$\overline{y} = \frac{\sum_i (y_i / \Delta y_i^2)}{\sum_i (1 / \Delta y_i^2)};$$

(d) transforming said error-weighted transformed signal to produce said error-weighted average by a method comprising using a transformation according to the equation $$\overline{x} = \frac{-(4 \cdot a^2 \cdot c^2 - a^2 \cdot e^{2a(\overline{y}-d)} + 2 \cdot a \cdot b^2 \cdot e^{a(\overline{y}-d)} - b^4)}{4 \cdot a^3 \cdot e^{a(\overline{y}-d)}}; \text{ and}$$

(e) outputting said error-weighted average $\overline{x}$ to a user interface device, a computer readable storage medium, or a local or remote computer system; or displaying said error-weighted average $\overline{x}$.

18. The method of claim 17, wherein said error $\Delta y_i$ of each said transformed signal $y_i$ is obtained according to the equation $$\Delta y_i = \frac{\Delta x_i}{\sqrt{c^2 + b^2 \cdot x_i + a^2 \cdot x_i^2}}$$

wherein $\Delta x_i$ is an error in said measured signal $x_i$.

19. The method of claim 18, wherein each said error $\Delta x_i$ is an error in said measured signal $x_i$ determined in said ith experiment.

20. The method of claim 18, wherein each said error $\Delta x_i$ is the larger of an error in said measured signal $x_i$ determined in said ith experiment or an error in said measured signal $x_i$ calculated according to the equation $$\Delta x_i = \sqrt{c^2 + b^2 \cdot x_i + a^2 \cdot x_i^2}.$$

21. A method for analyzing m signals $\{x\}_i$ measured in m experiments, wherein i=1, 2, . . . m, said method comprising (a) transforming each said signal $x_i$ into a transformed signal $y_i$ by a method comprising using a transformation $$y_i = \frac{\ln\left(\frac{b^2 + 2 \cdot a^2 \cdot x_i}{a} + 2 \cdot \sqrt{c^2 + b^2 \cdot x_i + a^2 \cdot x_i^2}\right)}{a} + d,$$

wherein a is the fractional error coefficient of said experiments, b is the Poisson error coefficient of said experiments, c is the averaged standard deviation of background noise of said experiments, and $$d = \frac{-\ln\left(\frac{b^2}{a} + 2 \cdot c\right)}{a};$$

(b) determining an error $\Delta y_i$ in each said transformed signal $y_i$;

(c) analyzing said transformed signals and their errors, thereby analyzing said m signals; and (d) outputting said transformed signal $y_i$ and/or said error $\Delta y_i$ to a user interface device, a computer readable storage medium, or a local or remote computer system; or displaying said transformed signal $y_i$ and/or said error $\Delta y_i$.

22. The method of claim 21, wherein for each measured signal $x_i$ said error in said transformed signal $y_i$ is obtained according to the equation $$\Delta y_i = \frac{\Delta x_i}{\sqrt{c^2 + b^2 \cdot x_i + a^2 \cdot x_i^2}}$$

wherein $\Delta y_i$ is said error in said transformed signal $y_i$, and wherein $\Delta x_i$ is an error in said measured signal $x_i$.

23. The method of claim 22, wherein said error in said measured signal $x_i$ is an error in said measured signal $x_i$ determined in said ith experiment.

24. The method of claim 22, wherein said error in measured signal $x_i$ is the larger of an error in said measured signal $x_i$ determined in said ith experiment or an error in said measured signal $x_i$ calculated according to the equation $$\Delta x_i = \sqrt{c^2 + b^2 \cdot x_i + a^2 \cdot x_i^2}.$$

25. The method of claim 24, wherein said step (c) is carried out by a method comprising performing ANOVA on said transformed signals and their errors.

26. The method of claim 25, wherein said step (c) is carried out by a method comprising performing a regression analysis on said transformed signals and their errors.

27. The method of claim 25, wherein said step (c) is carried out by a method comprising determining a variance of said transformed signals.

28. A method for determining if a measured signal x measured in an experiment is an outlier, comprising
(a) transforming said measured signal into a transformed signal y by a method comprising using a transformation according to the equation $$y = \frac{\ln\left(\frac{b^2 + 2 \cdot a^2 \cdot x}{a} + 2 \cdot \sqrt{c^2 + b^2 \cdot x + a^2 \cdot x^2}\right)}{a} + d,$$

wherein a is the fractional error coefficient of said experiment, b is the Poisson error coefficient of said experiment, and c is the standard deviation of background noise of said experiment, and $$d = \frac{-\ln\left(\frac{b^2}{a} + 2 \cdot c\right)}{a};$$

(b) determining an error in said transformed signal y;
(c) comparing said error in said transformed signal y with a predetermined threshold value, wherein said measured signal is identified as an outlier if said error in said transformed signal y is greater than said threshold value; and
(d) outputting a result of said comparing step (c) to a user interface device, a computer readable storage medium, or a local or remote computer system; or displaying a result of said comparing step (c).

29. The method of claim 28, wherein said error of said transformed signal y is determined according to the equation $$\Delta y = \frac{\Delta x}{\sqrt{c^2 + b^2 \cdot x + a^2 \cdot x^2}}$$

wherein $\Delta y$ is said error in said transformed signal y, and wherein $\Delta x$ is an error in said measured signal x.

30. The method of claim 28, wherein said error in measured signal x(k) is the larger of an error in said measured signal x determined in said experiment or an error in said measured signal x calculated according to the equation $$\Delta x = \sqrt{c^2 + b^2 \cdot x + a^2 \cdot x^2}.$$

31. A method of obtaining a difference of measured signals $\{x(k)\}$ measured in an experiment, wherein k=1, 2, said method comprising
(a) transforming said signals into transformed signals $\{y(k)\}$ by transforming each of said measured signals by a method comprising using a transformation according to $$y(k) = \frac{\ln\left(\frac{b^2 + 2 \cdot a^2 \cdot x(k)}{a} + 2 \cdot \sqrt{c^2 + b^2 \cdot x(k) + a^2 \cdot x(k)^2}\right)}{a} + d,$$

wherein a is the fractional coefficient of said experiment, b is the Poisson coefficient of said experiment, and c is the standard deviation of background noise of said experiment, and $$d = \frac{-\ln\left(\frac{b^2}{a} + 2 \cdot c\right)}{a};$$

(b) determining a difference between said transformed signals; and
(c) outputting said difference to a user interface device, a computer readable storage medium, or a local or remote computer system; or displaying said difference.

32. The method of any one of claims 1, 7, 13, 17, 21, 28 and 31, wherein said experiment is an experiment in which measurements of a plurality of cellular constituents are obtained.

33. The method of claim 32, wherein said experiment is a microarray experiment and said cellular constituents are mRNAs.

34. The method of claim 32, wherein said cellular constituents are proteins.

35. The method of claim 32, wherein said measured signal is measured fluorescence intensity.

36. A computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out the method of claim 35.

37. A computer system comprising
a processor, and
a memory coupled to said processor and encoding one or more programs, wherein said one or more programs cause the processor to carry out the method of claim 35.

38. The method of claim 32, wherein said measured signal is a difference between a measured fluorescence intensity of a probe and a measured fluorescence intensity of a reference probe.

39. A computer system comprising
a processor, and
a memory coupled to said processor and encoding one or more programs, wherein said one or more programs cause the processor to carry out the method of claim 38.

40. A computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out the method of claim 38.

41. A computer system comprising
a processor, and
a memory coupled to said processor and encoding one or more programs, wherein said one or more programs cause the processor to carry out the method of any one of claims 1, 7, 13, 17, 21, 28 and 31.

42. A computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out the method of any one of claims 1, 7, 13, 17, 21, 28 and 31.

* * * * *